US012643941B2

(12) United States Patent
Kauvar et al.

(10) Patent No.: US 12,643,941 B2
(45) Date of Patent: Jun. 2, 2026

(54) THERAPEUTIC PROTEIN FORMULATIONS COMPRISING ANTI-DNABII ANTIBODIES AND USES THEREOF

(71) Applicant: Trellis Bioscience, Inc., Redwood City, CA (US)

(72) Inventors: Lawrence M. Kauvar, San Francisco, CA (US); Stefan Ryser, Menlo Park, CA (US)

(73) Assignee: Trellis Bioscience, Inc., Redwood City, CA (US)

( * ) Notice: Subject to any disclaimer, the term of this patent is extended or adjusted under 35 U.S.C. 154(b) by 1191 days.

(21) Appl. No.: 17/565,134

(22) Filed: Dec. 29, 2021

(65) Prior Publication Data

US 2022/0204600 A1 Jun. 30, 2022

Related U.S. Application Data

(60) Provisional application No. 63/275,246, filed on Nov. 3, 2021, provisional application No. 63/132,252, filed on Dec. 30, 2020.

(51) Int. Cl.
| | |
|---|---|
| *C07K 16/18* | (2006.01) |
| *A61K 9/00* | (2006.01) |
| *A61K 31/427* | (2006.01) |
| *A61K 31/702* | (2006.01) |
| *A61K 39/40* | (2006.01) |
| *A61P 43/00* | (2006.01) |
| *C07K 16/12* | (2006.01) |

(52) U.S. Cl.
CPC ............ *C07K 16/18* (2013.01); *A61K 9/0078* (2013.01); *A61K 31/427* (2013.01); *A61K 31/702* (2013.01); *A61K 39/40* (2013.01); *A61P 43/00* (2018.01); *C07K 16/12* (2013.01)

(58) Field of Classification Search
CPC ....................................................... C07K 16/18
See application file for complete search history.

(56) References Cited

U.S. PATENT DOCUMENTS

| | | | |
|---|---|---|---|
| 9,018,158 B2 | 4/2015 | Onsoyen | |
| 10,233,234 B2 * | 3/2019 | Kauvar | .............. C07K 16/1228 |
| 2019/0000971 A1 | 1/2019 | Bakaletz | |
| 2020/0002409 A1 | 1/2020 | Goodman | |
| 2020/0069814 A1 * | 3/2020 | Zhao | ................... C07D 498/22 |

FOREIGN PATENT DOCUMENTS

WO 2020006528 1/2020

OTHER PUBLICATIONS

Wu et al (Journal of Molecular Biology vol. 294, pp. 151-162) (Year: 1999).*
MacCallum et al (Journal of Molecular Biology vol. 262, pp. 732-745) (Year: 1996).*
Skolnick et al (Trends in Biotechnology vol. 18, pp. 34-39) (Year: 2000).*
Casset et al (Bichemical and Biophysical Research Communications vol. 307, pp. 198-205) (Year: 2003).*
Vajdos et al (Journal of Molecular Biology vol. 320, pp. 415-428) (Year: 2002).*

* cited by examiner

*Primary Examiner* — Albert M Navarro
(74) *Attorney, Agent, or Firm* — FisherBroyles, LLP; Jason M. Pass; Adelaide K. Leitzel

(57) ABSTRACT

The present disclosure is directed to an aqueous therapeutic protein formulation including: (i) one or more therapeutic proteins, wherein the one or more therapeutic proteins include one or more anti-DNABII antibodies or antigen-binding fragments thereof in an amount ranging from 10 to 150 mg/mL; (ii) histidine buffer, (iii) NaCl, and (iv) an aqueous carrier, wherein a pH of the aqueous therapeutic formulation ranges from 5.5-8.0, and wherein the formulation is formulated for respiratory tract delivery and produces particles including the one or more therapeutic proteins upon aerosolization. Methods of generating an aerosol and treating biofilm-associated diseases or disorders, e.g., cystic fibrosis, ventilator-associated pneumonia, and acute exacerbations of chronic obstructive pulmonary disease or chronic bronchitis are also provided.

20 Claims, 8 Drawing Sheets

Specification includes a Sequence Listing.

THERAPEUTIC PROTEIN FORMULATIONS COMPRISING ANTI-DNABII ANTIBODIES AND USES THEREOF

SEQUENCE LISTING

A sequence listing comprising SEQ ID NOS: 1-6 is attached hereto. Each sequence provided in the sequence listing is incorporated herein by reference, in its entirety, for all purposes.

TECHNICAL FIELD

Formulations comprising therapeutic protein(s) suitable for aerosolization and treatment of biofilm-associated diseases or disorders, e.g., pulmonary biofilms, via administration to the respiratory tract are provided.

BACKGROUND

Monoclonal antibodies (mAbs) and other antibody-based therapies have proven successful for the treatment of cancers, inflammatory and autoimmune diseases. More recently, antibody cocktails have been developed that are effective for treating viral infections, e.g., COVID-19. For respiratory diseases, the airways are a possible route for the local delivery of drugs and this route is routinely used in clinical practice for the delivery of small drug molecules, such as β2-adrenoreceptor agonists, muscarinic antagonists, and corticosteroids for which reduced systemic exposure is a significant benefit. The airways have recently been evaluated for the delivery of biopharmaceuticals, including antibodies. However, administration of proteins by inhalation is rare and only one protein drug, dornase alfa (PULMOZYME®), a recombinant human DNase used for the treatment of cystic fibrosis, is currently approved.

The respiratory tract delivery of antibodies is challenging in terms of the formulation of biological agents for inhalation. A prerequisite for successful inhalation therapy is the efficient distribution and reliable deposition of sufficient numbers of aerosol particles in the respiratory tract region of interest. This is dependent on aerosol technology, the performance of the device (e.g., aerosol output, particle size) and the physical characteristics of the drug formulation. Nebulizers are the most widely used inhalers for generating aerosols from protein solutions. However, while nebulizers are recognized as useful for generating aerosols from protein solutions, the effect of aerosolization and protein formulation on the molecular integrity of an active antibody may prohibit effective inhalation therapies. Like other therapeutic proteins, antibodies may undergo conformational changes, potentially decreasing their biological activity. Further, antibodies are susceptible to various stresses, such as high temperature, extreme pH, shear stress and freezing. Aerosol formation involves the dispersion/suspension of solid material or liquid droplets in a gaseous medium. This process is associated with physical stresses likely to induce changes in protein conformation. The development of inhaled antibody treatments is therefore a challenge for drug formulators.

Improved management of lung infections in ventilator-associated pneumonia (VAP), acute exacerbation of chronic bronchitis, chronic obstructive pulmonary disease (COPD), and cystic fibrosis (CF) has long been a priority in medical practice and is even more critical now due to COVID-19. These recurrent bronchial infections are believed to be due to re-seeding of the infection by bacteria shed from a biofilm protected reservoir in the nasopharynx [Fothergill J L, Neill D R, Loman N, Winstanley C, Kadioglu A. *Pseudomonas aeruginosa* adaptation in the nasopharyngeal reservoir leads to migration and persistence in the lungs. *Nat Commun.* 5:4780 (2014).]. As a result, existing antibiotics are grossly insufficient to manage these infections.

VAP occurs in 10-30% of all mechanically-ventilated patients with estimated incidence rate of ~5 cases per 1,000 ventilator days [Skrupky L P, McConnell K, Dallas J, Kollef M H. A comparison of ventilator-associated pneumonia rates as identified according to the National Healthcare Safety Network and American College of Chest Physicians criteria. *Crit Care Med* 40 (1):281-4 (2012)].

Phenomenologically, oropharyngeal (OP) colonization and VAP are tightly linked [Messika J, La Combe B, Ricard J D. Oropharyngeal colonization: epidemiology, treatment and ventilator-associated pneumonia prevention. *Ann Transl Med.* 6 (21):426 (2018).]. At initial ICU admission, >30% of patients carry an OP infection, with a majority acquiring such an infection while in the ICU. OP colonization is a major risk factor for VAP: 23% of patients with OP colonization evolved to a confirmed VAP (with the same pathogen) vs. only 3.3% of patients without OP colonization (P<0.0001). A 2008 study of the Canadian health care system provides an estimate for the cost burden of OP [Muscedere J G, Martin C M, Heyland D K. The impact of ventilator-associated pneumonia on the Canadian health care system. *J Crit Care* 23 (1):5-10 (2008)]. Extrapolated to the US, the current annual cost of care associated with VAP is ~$1 billion.

COVID-19 patients are significantly more likely to develop VAP than patients without COVID (p=0.0015) [Maes M, Higginson E, Pereira-Dias J, Curran M D, Parmar S, Khokhar F, Cuchet-Lourengo D, Lux J, Sharma-Hajela S, Ravenhill B, Hamed I, Heales L, Mahroof R, Soderholm A, Forrest S, Sridhar S, Brown N M, Baker S, Navapurkar V, Dougan G, Bartholdson Scott J, Conway Morris A. Ventilator-associated pneumonia in critically ill patients with COVID-19. *Crit Care.* 25 (1):25 (2021)], with high recurrence (79% in a study of 50 patients) [Luyt C E, Sahnoun T, Gautier M, Vidal P, Burrel S, Pineton de Chambrun M, Chommeloux J, Desnos C, Arzoine J, Nieszkowska A, Bréchot N, Schmidt M, Hekimian G, Boutolleau D, Robert J, Combes A, Chastre J. Ventilator-associated pneumonia in patients with SARS-CoV-2-associated acute respiratory distress syndrome requiring ECMO: a retrospective cohort study. *Ann Intensive Care.* 10 (1):158 (2020)].

Bacterial infection can cause acute exacerbation of chronic bronchitis (AECB) and of chronic obstructive pulmonary disease (COPD) with significant adverse impact, and high recurrence rate [Ritchie A I, Wedzicha J A. Definition, Causes, Pathogenesis, and Consequences of Chronic Obstructive Pulmonary Disease Exacerbations. *Clin Chest Med.* 41 (3):421-438 (2020)]. Direct costs of treatment in the US for these chronic conditions exceed $30 billion annually, with exacerbations estimated to account for over half of these costs; about half of the exacerbations are due to bacterial infection. Recurrence is common, with about a quarter of patients experiencing such an event within 2 months. Exacerbations are the predominant cause of mortality in these patients. Each new exacerbation requiring hospitalization raises the risk of death, and decreases the interval between hospitalizations. In a study conducted in Canada, mortality was 75% within 7.7 years [Suissa S, Dell'Aniello S, Ernst P. Long-term natural history of chronic obstructive pulmonary disease: severe exacerbations and mortality. *Thorax* 67 (11):957-63 (2012)].

Chronic bronchitis has been recognized as a subset of COPD for about two decades [Brunton S, Carmichael B P, Colgan R, Feeney A S, Fendrick A M, Quintiliani R, Scott G. Acute exacerbation of chronic bronchitis: a primary care consensus guideline. *Am J Manag Care.* 10 (10):689-96 (2004)]. Such patients are characterized by an irreversible reduction in maximal airflow velocity along with a productive cough on most days of the month for 3 months or more over 2 consecutive years. Acute exarcebation is characterized by worsening airflow and associated symptoms including shortness of breath, increased sputum production, and increased sputum purulence. Most (80%) cases of AECB are due to infection, with half due to bacteria. Clinically, increased dyspnea, cold symptoms, and sore throat are generally associated with a viral exacerbation, whereas increased sputum production or purulence, associated with neutrophilic inflammation, is generally bacterial. The predominant aerobic bacteria are: *Pseudomonas aeruginosa, Streptococcus pneumoniae, Haemophilus influenzae,* and *Moraxella catarrhalis.* Low dose, short duration treatment with corticosteroids is beneficial in managing acute symptoms [Woods J A, Wheeler J S, Finch C K, Pinner N A. Corticosteroids in the treatment of acute exacerbations of chronic obstructive pulmonary disease. *Int J Chron Obstruct Pulmon Dis.* 9:421-30 (2014)]. Treatment with mucolytics leads to only a small reduction in the likelihood of having an acute exacerbation [Poole P, Sathananthan K, Fortescue R. Mucolytic agents versus placebo for chronic bronchitis or chronic obstructive pulmonary disease. *Cochrane Database Syst Rev.* 5 (5):CD001287 (2019)]. Biofilm has been increasingly implicated in the pathology [Weeks J R, Staples K J, Spalluto C M, Watson A, Wilkinson T M A. The Role of Non-Typeable Haemophilus influenzae Biofilms in Chronic Obstructive Pulmonary Disease. *Front Cell Infect Microbiol.* 11:720742 (2021)].

Most murine studies of *Pseudomonas aeruginosa* respiratory infection have been acute pneumonia models that result in either rapid bacterial clearance or development of sepsis and host death. Such models are more appropriate to test bactericidal antibiotics than a product that acts by disrupting biofilms. A longer-term model uses agar beads impregnated with bacteria to mimic chronic infection, but this model does not closely reflect the natural respiratory route of infection. Spread of bacteria to the alveoli is difficult to achieve and the alginate beads may cause mechanical blocking and damage to the bronchi. Further, the high alginate concentration masks the role of extracellullar DNA as a primary biofilm structural component, which makes such a model inappropriate for evaluation of a product that targets the proteins holding extracellular DNA in place.

To address the shortcomings of these models, a Mouse Respiratory Chronic Infection Model (MRCIM) was established at the Institute of Infection & Global Health, University of Liverpool [Fothergill et al.]. In this model, *P. aeruginosa* is introduced intranasally and establishes stable colonization of the nasopharynx and infection of the lungs over a 28-day period. Early gene expression and adaptation are similar to an in vitro biofilm model. The expression of these biofilm-related genes supports previous work in which *P. aeruginosa* has been found to form biofilms in the paranasal sinuses [Johansen et al., Colonisation and infection of the paranasal sinuses in cystic fibrosis patients is accompanied by a reduced PMN response. *J Cyst Fibros.* 11 (6):525-31 (2012)]. Bacteria introduced via this natural inoculation establish colonization in the nasopharynx enabling adaptation and migration down into the lungs. DNABII proteins are found in sputum of cystic fibrosis patients [Gustave J E, Jurcisek J A, McCoy K S, Goodman S D, Bakaletz L O. Targeting bacterial integration host factor to disrupt biofilms associated with cystic fibrosis. *J Cyst Fibros.* 12 (4):384-9 (2013).]

As disclosed in [Vigil et al. Airway delivery of anti-influenza monoclonal antibodies results in enhanced antiviral activities and enables broad-coverage combination therapies. *J Virol* 94:e00052-20 (2020)] CF-404, which is a mixture of three monoclonal antibody products, neutralizes all circulating strains of influenza, and that the anti-influenza antibody mixture is as effective when delivered by nebulizer (NEB) as by intranasal delivery (IN) and more efficient than by intraperitoneal (IP) delivery. In the Vigil et al. reference, the delivery of mAbs to the respiratory system was tested using a commercially available nebulizer that produces approximately 2 um droplets for delivery to the lungs (Aerogen). In brief, mice were infected with 3×LD50 of H1N1 virus (strain A/Puerto Rico/8/34) and treatment group cohorts (n=5) dosed at 24 hr postinfection with CF-404 (a mixture of 3 mAbs neutralizing all currently circulating Influenza A and B strains) delivered intranasally (IN), via inhalation of nebulized material (NEB), or intraperitoneally (IP). No decrease was detected in antibody activity for NEB compared to IN, and each showed comparable efficacy to IP at ~20-fold lower dose. Antibiotics alone have been delivered clinically by inhalation or instillation for both VAP and CF, but only with partial success since antibiotics do not remove the biofilm reservoir.

However, it has not been shown up to this point that the anti-DNABII antibodies provided for herein would likely be efficacious to treat biofilm associated with pulmonary infection. As previously described [U.S. Pat. No. 10,233,234], certain monoclonal antibodies against the DNABII family of DNA binding proteins (implicated in retaining extracellular DNA within the biofilm matrix) are effective when delivered systemically for treatment of biofilm associated infections.

BRIEF SUMMARY OF THE INVENTION

The present disclosure is directed to a therapeutic protein formulation, typically comprising antibodies, which is particularly suitable for treating pulmonary biofilms. The formulation, which may be aerosolized and delivered into the respiratory tract, reduces the possibility of e.g., coughing and irritation of the lung mucosa. Moreover, the formulation is particularly useful for stabilizing therapeutic proteins, such as antibodies, thereby mitigating loss of activity during storage or aerosolization. Furthermore, the formulation may include relatively high concentrations of therapeutic protein, which reduces the need for large volumes and prolonged aerosolization times and, thus, typically promotes patient compliance. These and other unexpected benefits of the present formulation are described herein.

In one aspect, the present disclosure is directed to an aqueous therapeutic protein formulation comprising: (i) one or more therapeutic proteins, wherein the one or more therapeutic proteins comprise one or more anti-DNABII antibodies or antigen-binding fragments thereof in an amount ranging from 10 to 150 mg/mL; (ii) histidine buffer, (iii) NaCl, and (iv) an aqueous carrier, wherein a pH of the aqueous therapeutic formulation ranges from 6.0-8.0, and wherein the formulation is formulated for respiratory tract delivery and produces particles comprising the one or more therapeutic proteins upon aerosolization. In certain embodiments, the aqueous therapeutic protein formulation further comprises a surfactant, such as a polysorbate.

Also provided herein is a method of generating an aerosol comprising the step of: nebulizing the aqueous therapeutic protein of any one of the preceding using a nebulizer to obtain an aerosol.

In another aspect, the present disclosure provides a method for the therapeutic and/or prophylactic treatment of biofilm-associated bacterial infections, which method comprises administering the aqueous therapeutic protein formulation to a subject in need thereof.

In still another aspect, the present disclosure provides a method for the therapeutic and/or prophylactic treatment of biofilm-associated bacterial infections, which method comprises administering the aqueous therapeutic protein formulation adjunctively with an antibiotic to a subject in need thereof.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIGS. 2A-2D are photomicrographs of a stainless steel needle coated with biofilm, stained with controls (A: untreated infection; B: stained with fluorescent label alone; C: stained with fluorescent label attached to isotype control mAb not reactive with DNABII) and D: with fluorescent label attached to TRL1068, a mAb binding to DNABII.

DETAILED DESCRIPTION

Figure 1:
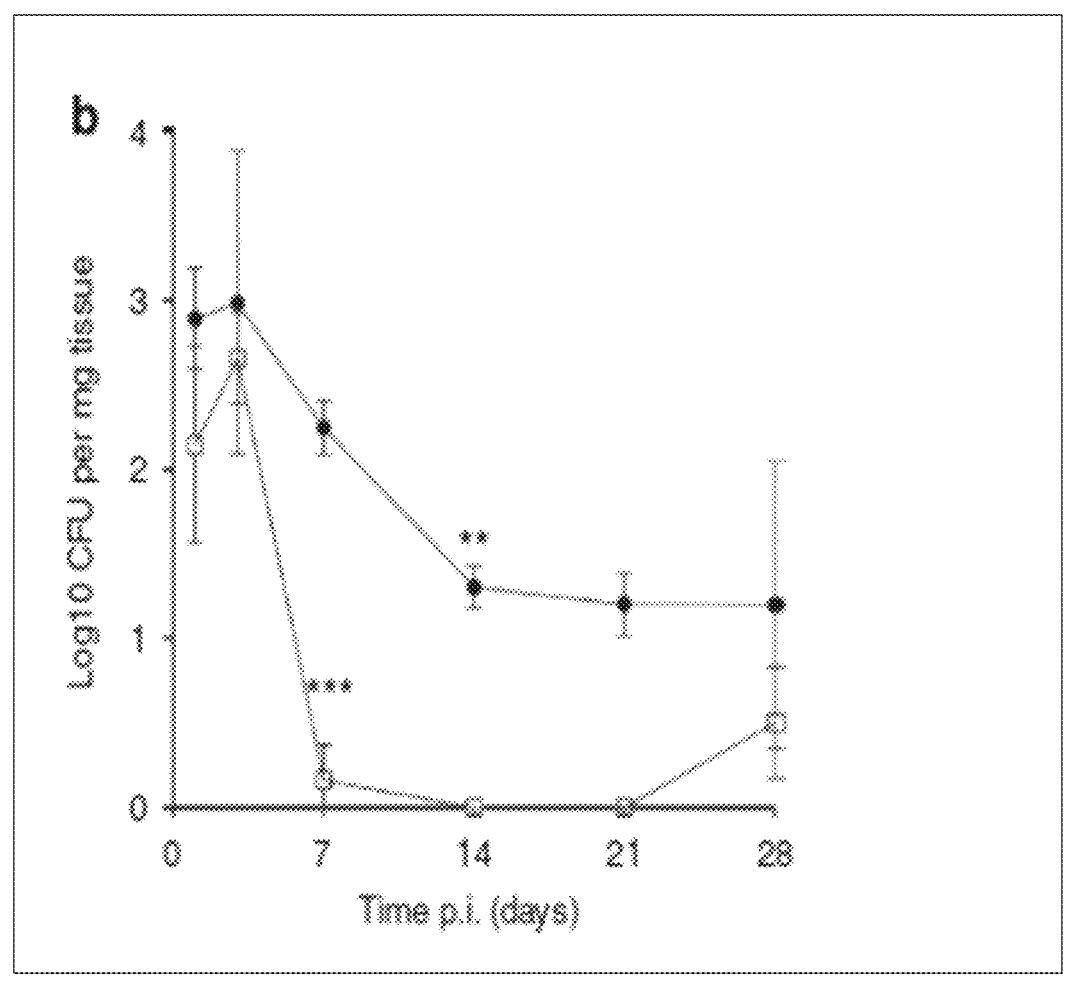
FIG. 1 is a graph depicting *P. aeruginosa* in the murine lung and nasopharynx. *P. aeruginosa* colony forming units present in the lung (white squares) and nasopharynx (black circles) of mice for 28 days following intranasal inoculation with LESB65 [1].

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range. The term about is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

Definitions

As used herein, "during storage," refers to a formulation that once prepared, is not immediately used; rather, following its preparation, it is packaged for storage, either in a liquid form, in a frozen state, or in a dried form (for later reconstitution into a liquid form).

As used herein, "aggregate" refers to a physical interaction between protein molecules, which results in the formation of covalent or non-covalent dimers or oligomers, which may remain soluble, or form insoluble aggregates that precipitate out of solution. An "aggregate" also refers to degraded and/or fragmented therapeutic proteins, such as degraded and/or fragmented antibodies or antigen-binding fragments thereof as herein described.

As used herein, a "particle" refers to liquids, e.g., droplets.

As used herein, "aerosolization" refers to the production of an aerosol (e.g., a suspension of micron scale liquid droplets) by the transformation of a formulation into small particles or droplets, e.g., by use of an aerosol delivery system, e.g., nebulizer, as described herein.

As used herein, "nebulize" and "nebulization" refer to the conversion of a liquid into a mist or fine spray by a nebulizer as described herein.

As used herein, a "pharmaceutical formulation" refers to formulations which are in such a form as to permit the biological activity of the active ingredients to be effective, and, therefore, may be administered to a subject for therapeutic use as described herein.

As used herein, the term "protein" may be used herein interchangeably with the term "polypeptide" and, as used herein, encompasses a peptide, a polypeptide, a protein, and a fusion protein. Proteins may be made by recombinant or synthetic methods.

As used herein, the terms "subject" and "patient" are used interchangeably. As used herein, the terms "subject" and "subjects" refer to an animal, typically a mammal including a non-primate (e.g., a cow, pig, horse, cat, dog, rat, and mouse) and a primate (e.g., a monkey, such as a cynomolgus monkey, chimpanzee, baboon, and a human), and more typically a human.

As used herein, the terms "therapeutic agent" and "therapeutic agents" refer to any agent(s), such as a drug or protein including antibodies and antigen-binding fragments thereof as described herein that can be used in the prevention, treatment and/or management of one or more diseases and/or disorders.

As used herein, the term "therapeutically effective amount" refers to the amount of a therapeutic agent, which is sufficient to reduce the severity of one or more diseases and/or disorders.

As used herein, the term "excipient" refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine, histidine), surfactants (e.g., sodium dodecyl sulfate (SDS), polysorbates such as Tween 20 and Tween 80, poloxamers such as Pluronics, and other nonionic surfactants such as polyethylene glycol) (PEG)), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., 1990, Mack Publishing Co., Easton, Pa.), which is incorporated by reference herein in its entirety.

As used herein, an "antibody" describes an immunoglobulin whether natural or partly or wholly synthetically produced. The term also encompasses "antigen-binding fragments" as described herein. The term encompasses polyclonal, monoclonal, monospecific monoclonal antibodies, multispecific antibodies such as bi-specific monoclonal antibodies or tri-specific monoclonal antibodies, isolated monoclonal antibodies, recombinant monoclonal antibodies, and isolated human or humanized monoclonal antibodies, the last mentioned described in further detail in U.S. Pat. Nos. 4,816,397 and 4,816,567, which are each incorporated by reference in its entirety. Immunoglobulin molecules can be of any class (e.g., IgG, IgE, IgM, IgD, IgA, and IgY), or subclass (e.g., IgGI, IgG2, IgG3, IgG4, IgAI, and IgA2). Preferred antibodies are of the IgG class. The term "antibody(ies)" includes a wild type immunoglobulin (Ig) molecule, generally comprising four full length polypeptide chains, two heavy (H) chains and two light (L) chains; including full length functional mutants, variants, or derivatives thereof, which retain the essential epitope binding features of an Ig molecule.

As used herein, an "antigen-binding fragment" refers to a molecule other than an intact antibody that comprises a portion of an intact antibody that binds the antigen to which the intact antibody binds. Examples of antibody-binding fragments include but are not limited to (i) a Fab fragment; (ii) a F(ab')2 fragment; (iii) a heavy chain portion of a Fab (Fd) fragment, which comprises VH and CH1 domains; (iv) a single chain Fab (scFAb) which is described, for example, in U.S. Publication No. 2007/0274985 and is herein incorporated by reference in its entirety; (v) a Fab'-like fragment, which differs from a Fab fragment in that the Fab'-like fragment is slightly larger having more heavy chain and typically having one or more additional sulfhydryl groups on its heavy chain; (vi) a domain antibody (dAb) fragment, which comprises a single variable domain; (vii) a camelid antibody; (viii) a variable fragment (Fv) fragment, which comprises the VL and VH domains of a single arm of an antibody, (ix) a single chain Fv fragment (scFv) wherein a VH domain and a VL domain are linked by a linker that allows the two domains to associate to form an antigen binding site; (x) multivalent antibody fragments (scFv dimers, trimers and/or tetramers; (xi) a diabody, which is a bivalent, bispecific antibody in which VH and VL domains are expressed on a single polypeptide chain, but which uses a linker that is too short to allow for pairing between the two domains on the same chain, thereby forcing the domains to pair with the complementarity domains of another chain and creating two antigen binding sites; (xii) a linear antibody, which comprises a pair of tandem Fv segments (VH—CH1-VH—CH1) which, together with complementarity light chain polypeptides, form a pair of antigen binding regions; (xiii) a minibody, which is a bivalent molecule comprising an scFv fused to constant immunoglobulin domains, CH3 or CH4, wherein the constant CH3 or CH4 domains serve as dimerization domains; and (ix) other non-full length portions of heavy and/or light chains, or mutants, variants, or derivatives thereof, alone or in any combination.

As used herein, "monoclonal antibody" refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. A monoclonal antibody thus typically displays a single binding affinity for any antigen with which it immunoreacts. In contrast to polyclonal antibody preparations, which typically include different antibodies directed against different determinants (epitopes), each monoclonal antibody of a monoclonal antibody preparation is directed against a single determinant on an antigen. The modifier "monoclonal" indicates the character of the antibody as being obtained from a substantially homogeneous population of antibodies and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies described, for example, in WO 2014/152841, which is herein incorporated by reference in its entirety. A specific embodiment uses the antibody or antibodies described in U.S. Pat. No. 10,233,234.

As used herein, "Fab fragment" refers to an antibody fragment comprising a light chain fragment comprising a VL domain and a constant domain of a light chain (CL), and a VH domain and a first constant domain (CH1) of a heavy chain. Fab and F(ab')2 portions of antibody molecules may be prepared by the proteolytic reaction of papain and pepsin, respectively, on substantially may be prepared by the proteolytic reaction of papain and pepsin, respectively, on substantially intact antibody molecules by methods that are well-known or may be prepared synthetically or recombinantly. Fab' antibody molecule portions are also well-known and may be produced from F(ab')2 portions followed by reduction of the disulfide bonds linking the two heavy chain portions as with mercaptoethanol, and followed by alkylation of the resulting protein mercaptan with a reagent such as iodoacetamide.

As used herein, "Fc domain" refers to a C-terminal region of an immunoglobulin heavy chain that contains at least a portion of the constant region. For example, in natural IgG antibodies, the Fc domain is composed of two identical protein fragments, derived from the second and third constant domains of the antibody's two heavy chains.

As used herein, "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively.

As used herein, "epitope" refers to a region of an antigen (e.g., polypeptide) that is bound by the antigen-binding site of an antibody. In certain embodiments, an epitope determinant includes chemically active surface groupings of molecules such as amino acids, sugar side chains, phosphoryl, or sulfonyl, and, in certain embodiments, may have specific three-dimensional structural characteristics, and or specific charge characteristics.

As used herein, "percent amino acid sequence identity" refers to the percentage of amino acid residues in a candidate sequence that are identical with the amino acid residues in the reference polypeptide sequence, such as an antibody comprising a heavy chain and a light chain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available software such as BLAST or software available commercially, for example from DNASTAR. Two or more polypeptide sequences can be anywhere from 0-100% identical, or any integer value there between. In the context of the present disclosure, two polypeptides are "substantially identical" when at least 80% of the amino acid residues (such as at least about 85%, at least about 90%, at least about 92.5%, at least about 95%, at least about 98%, or at least about 99%) are identical. The term "percent (%) amino acid sequence identity" as described herein applies to peptides as well. Thus, the term "substantially identical" will encompass mutated, truncated, fused, or otherwise sequence-modified variants of antibodies, antigen-binding fragments thereof, as well as polypeptides, such as antibodies, with substantial sequence identity (e.g., at least 80%, at least 85%, at least 90%, at least 92.5%, at least 95%, at least 98%, or at least 99% identity as measured for example by one or more methods referenced above) as compared to the reference (wild type or other intact) polypeptide, such as an antibody.

As used herein, two amino acid sequences, such as two antibodies, e.g., comprising a heavy chain, are "substantially homologous" when at least about 80% of the amino acid residues (such as at least about 85%, at least about 90%, at least about 92.5%, at least about 95%, at least about 98%, or at least about 99%) are identical, or represent conservative substitutions. The sequences of the polypeptides, such as the antibodies of the present disclosure, are substantially homologous when one or more, such as up to 10%, up to 15%, or up to 20% of the amino acids of the polypeptide, such as the antibodies described herein, are substituted with a similar or conservative amino acid substitution, and wherein the resulting peptides have at least one activity (e.g., ability to bind a specific epitope, neutralizing activity) of the reference polypeptide, such as an activity of an antibody described herein.

As used herein, a "conservative amino acid substitution" refers to one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

As used herein, "preventing" or "prevention" refers to a reduction in risk of acquiring or developing a disease or disorder (i.e., causing at least one of the clinical symptoms of the disease not to develop) in a subject that may be exposed to a disease causing agent, or predisposed to the disease in advance of disease onset.

As used herein, "prophylaxis" is related to and encompassed in the term "prevention" and refers to a measure or procedure, the purpose of which is to prevent, rather than to treat or cure a disease.

As used herein "intranasal" refers to administering, e.g., a formulation of the disclosure, within or via the nose or nasal structures or airway delivery, for example as nasal drops or by inhalation. The term intranasal as used herein is not intended to be limited to or to imply limitation to administration directly or specifically or solely via the nose or nasal cavity, particularly in serving to exclude other means of administration whereby drug, agent, antibody, fragment, composition is delivered or otherwise provided to, deposited in or at or otherwise distributed to the respiratory tract.

As used herein, "inhalation" refers to taking in, particularly in the context of taking in or administering/being administered an agent or compound, including an antibody, or a composition comprising such, whereby the agent, compound, antibody, including as comprised in the formulation, is delivered to all or part of the respiratory tract. Inhalation may occur via the nose or via the mouth, or via direct administration to the lower respiratory tract as in intratracheal administration. Thus, inhalation may include nose only or primarily, intranasal, inhaling via the mouth, oral inhalation, intratracheal inhalation, intratracheal instillation. Thus, inhalation provides for and contemplates any means of administration to the respiratory tract exclusively, specifically or preferentially, including the upper and/or lower respiratory tract, whereby the drug, agent, composition or antibody reaches or is deposited at or in the respiratory tract exclusively, specifically or preferentially, including the upper and/or lower respiratory tract.

As used herein, the term "treating" or "treatment" refers to any process, action, application, therapy, or the like, wherein a subject, such as a human being, is subjected to medical aid with the object of curing a disorder, eradicating a pathogen, or improving the subject's condition, directly or indirectly. Treatment also refers to reducing incidence, alleviating symptoms, eliminating recurrence, preventing recurrence, preventing incidence, reducing the risk of incidence, improving symptoms, improving prognosis, or combinations thereof. "Treatment" may further encompass reducing the propagation of a pathogen in a subject and thereby controlling or reducing a pathogenic infection, such as a biofilm-associated disease(s) or disorder(s) in a subject or biofilm-associated contamination of an organ, tissue, or environment.

As used herein, the term "upper airways" or "upper respiratory tract" generally refers to the nasal cavity, pharynx, and larynx regions.

As used herein, the term "lower airways" or "lower respiratory tract" generally refers to the trachea, primary bonchi and lung regions.

Formulations

The present disclosure is directed to a therapeutic protein formulation, typically for respiratory tract delivery. In some embodiments, the present therapeutic protein formulation (also referred to herein as a "formulation", a "composition of matter" or a "composition") is a liquid formulation, more typically an aqueous formulation. As used herein, an "aqueous formulation" is a formulation in which the solvent is water. In some embodiments, the present formulation is a lyophilized formulation, a freeze-dried formulation or a spray-dried formulation, which may be reconstituted as a liquid, e.g., an aqueous formulation, prior to administration to a subject.

In some embodiments, the present formulation is useful for respiratory tract delivery via aerosolization. Accordingly, the present formulations have a viscosity that is compatible with aerosolization. Typically, the present formulation exhibits a dynamic viscosity in the range of about 0.8 mPa s to about 17.0 mPa s at a temperature of about 20° C., such as about 2 to 8 mPa s, such as about 3 to 7 mPa s, such as about 3 to 4 mPa s.

Generally, high concentrations of therapeutic protein are used in the present formulation. High doses of therapeutic protein are typical in the disclosure, as the volume to be aerosolized may thereby be minimized in order to keep the aerosolization time as short as possible, typically to promote patient compliance. Typically, the concentration of therapeutic protein in the present formulation ranges from about 5 mg/mL to about 150 mg/mL, such as from about 10 mg/mL to about 100 mg/mL, such as from about 30 mg/mL to about 70 mg/mL. More typically, the concentration of therapeutic protein in the present formulation is about 20 mg/mL.

Generally, the present therapeutic protein formulation is a stable formulation. A "stable" formulation is one in which the therapeutic protein in the formulation essentially retains its physical stability and/or chemical stability and/or biological activity upon storage, including storage in a reservoir of an aerosolization device, such as a nebulizer as described herein or during aerosolization. A protein "retains its physical stability" in a formulation if it shows little to no change in aggregation, precipitation and/or denaturation as observed by, for example, visual examination of color and/or clarity, or as measured by UV light scattering (measures visible aggregates) or size exclusion chromatography (SEC).

A protein "retains its chemical stability" in a formulation if the protein is not degraded. Chemical stability can be assessed by detecting and quantifying chemically altered forms of the protein. Chemical alteration may involve size modification (e.g., clipping), which can be evaluated, for example, using SEC, sodium dodecyl sulfate-polyacrylamide gel electrophoresis (SDS-PAGE) and/or matrix-assisted laser desorption ionization/time-of-flight mass spectrometry (MALDI/TOF MS). Other types of chemical alteration include charge alteration (e.g., occurring as a result of deamidation), which can be evaluated by e.g., ion-exchange chromatography.

The therapeutic protein of the present formulation, which typically comprises one or more antibodies as described herein, "retains its biological activity" in a formulation if the biological activity of, e.g., the antibody, at a given time, such as before storage or aerosolization, is within about 10% of its biological activity exhibited at the time the formulation is prepared as determined, e.g., in an antigen-binding assay, such as an enzyme-linked immunosorbent assay (ELISA) assay.

The term "stable" with respect to the formulation of the present disclosure during storage or aerosolization is understood to mean that the therapeutic protein of the present formulation does not lose more than 15%, or more typically 10%, or even more typically 5%, and yet even more typically 3% of its biological activity during storage relative to its activity at the beginning of storage or prior to aerosolization.

In some embodiments, the present formulation results in a reduction in the amount of aggregation of the therapeutic protein during storage, including storage in a reservoir of an aerosolization device, such as a nebulizer or during aerosolization in comparison to the amount of aggregation of the therapeutic protein during storage or aerosolization in the absence of the stabilizing agents as herein described.

Aggregates may be formed, for example, because of exposure to elevated temperatures. By "elevated temperature" is meant any temperature above the temperature at which the formulation of the disclosure comprising the present therapeutic antibodies is normally stored. The normal storage temperature is between about −70° C. and 8° C., typically about −20° C., or about 4° C. and 8° C., more typically between about 4° C. and 6° C. and even more typically at a temperature of about 4° C. In some embodiments, the present therapeutic protein formulation provided herein is also stabilized at room temperature (i.e., between 20° C. and 25° C.).

Further causes for the formation of aggregates during storage are due to the inherent tendency of therapeutic proteins, such as the therapeutic proteins described herein, to form aggregates. Without being bound by theory, it is assumed that aggregate formation of the present therapeutic proteins may lead to a loss of activity.

Aggregate formation during storage or aerosolization can be assessed by various analytical and/or immunological methods known in the art including but not limited to e.g. size exclusion chromatography (SE-HPLC), subvisible particle counting, analytical ultracentrifugation (AUC), dynamic light scattering (DLS), static light scattering (SLS), elastic light scattering, OD320/OD280, Fourier Transform Infrared Spectroscopy (FTIR), circular dichroism (CD), urea-induced protein unfolding techniques, intrinsic tryptophan fluorescence and/or differential scanning calorimetry techniques. Typically, SE-HPLC is used to assess the molecular size distribution and the relative amounts of the present therapeutic proteins and impurities during storage. SE-HPLC methods are known to the skilled person.

In some embodiments, the present therapeutic proteins include no more than 20%, no more than 10%, no more than 7%, no more than 6%, no more than 5%, no more than 4%, no more than 3%, no more than 2%, no more than 1%, or no more than 0.5% aggregation by weight of protein during storage in comparison to the aggregation by weight of the therapeutic protein at the beginning of storage or aerosolization.

In some embodiments, the present therapeutic protein formulation provided herein is stored between about 4° C. and 8° C. for an extended period of time. In some embodiments, the present therapeutic protein formulation is stable when stored between about 4° C. and 8° C. for at least about 1 month. In some embodiments, the present formulation is stable when stored between about 4° C. and 8° C. for at least about 3 months. In yet other embodiments, the present formulation is stable when stored between about 4° C. and 8° C. for at least 6 months, such as at least one year, such as at least two years.

In some embodiments, the present therapeutic protein formulation provided herein is stored between about –70° C. and –20° C. for an extended period of time. In some embodiments, the present therapeutic protein formulation is stable when stored between about –70° C. and –20° C. for at least about 1 month. In some embodiments, the present formulation is stable when stored between about –70° C. and –20° C. for at least about 3 months. In yet other embodiments, the present formulation is stable when stored between about –70° C. and –20° C. for at least 6 months, such as at least one year, such as at least two years.

In some embodiments, the present therapeutic protein of the formulation of the disclosure comprises a stabilizing agent, which comprises a charged amino acid, having a net charge at a pH between about 5.0 and 8.0, such as about 6.0 to about 6.5, such as about 6.0 in solution. The term "about" when used in the context of pH value/range refers to a numeric value having a range of +/–25% around the cited value. Without being limited by theory, the presence of the charged amino acids allows for the preparation of highly concentrated therapeutic protein formulations as described herein. In some embodiments, the charged amino acid is arginine, glutamate or histidine. Typically, the amino acid is histidine.

The term "net charge", in reference to an amino acid as used herein, means that positive and negative charges on the surface of the amino acid are not zero. The net charge depends on pH. At a specific pH, the positive and negative charges will be balanced and the net charge will be zero, i.e., the isoelectric point.

Typically, the stabilizing agent comprises a histidine buffer. As used herein, a "buffer" refers to a buffered solution that resists changes in pH by the action of its acid-base conjugate components. As used herein, a "histidine buffer" is a buffer comprising histidine ions. Examples of histidine buffers include histidine chloride, histidine acetate, histidine phosphate and histidine sulfate. In some embodiments, the histidine buffer minimizes irritation to the lungs. In some embodiments, the histidine buffer excludes histidine acetate since this buffer may irritate the lungs. The most typical histidine buffer in the present formulation is histidine chloride. In a typical embodiment, the histidine chloride buffer is prepared by titrating L-histidine (free base, solid) with hydrochloric acid (liquid) or titrating Histidine buffer with Histidine chloride buffer solution to a predetermined pH. Typically, the histidine buffer or histidine-chloride buffer is at a pH of about 5.5 to about 7.5, typically a pH of about 6.0 to about 6.5, most typically about 6.0.

It is to be understood that the pH can be adjusted as necessary to maximize stability and solubility of the therapeutic protein in a particular aqueous formulation. The pH value of the present formulations may be adjusted by the addition of acidic agents or basic agents. The pH may be raised, or made more alkaline, by addition of an alkaline agent such as sodium hydroxide, ammonium hydroxide, potassium hydroxide, sodium carbonate, sodium bicarbonate or combinations thereof. Suitable acids for use as pH adjusting agents include, for example, hydrochloric acid, phosphoric acid, phosphorous acid, citric acid, glycolic acid, lactic acid, acetic acid, benzoic acid, malic acid, oxalic acid, tartaric acid, succinic acid, glutaric acid, valeric acid and the like. Typically, hydrochloric acid is used to adjust the pH of the present formulation if needed.

In typical embodiments, histidine is present in the formulation at a concentration ranging from 5 mM to 30 mM, such as between 10 mM and 25 mM, such as between 15 mM and 25 mM. In some embodiments, the concentration of histidine in the present formulation is 5.0±0.5 mM, 10.0±1 mM, 15.0±1.5 mM, 20±2 mM, 25±2.5 mM, 30±5 mM or lower. In other embodiments, the concentration of histidine in the formulation is 5.0±0.5 mM, 10.0±1 mM, 15.0±1.5 mM, 20±2 mM, 25±2.5 mM, 30±5 mM or higher. More typically, the concentration of histidine in the formulation is 20.0±0.5 mM, 20.0±1 mM, 20±1.5 mM, 20±2 mM, 20±2.5 mM or 20±5 mM. Even more typically, the concentration of histidine in the formulation is 20 mM.

It will be understood by one skilled in the art that the present therapeutic formulation may be isotonic or slightly hypotonic with human blood, i.e. the present therapeutic formulation of the disclosure has essentially the same or a slightly lower osmotic pressure as human blood. Such isotonic or slightly hypotonic formulation generally has an osmotic pressure from about 240 mOSm/kg to about 320 mOSm/kg, such as about 240 mOSm/kg or higher, 250 mOSm/kg or higher or 260 mOSm/kg or higher. Osmotic pressure can be measured, for example, using a vapor pressure or ice-freezing type osmometer.

Tonicity of the present formulation can be adjusted by the use of a tonicity adjuster. "Tonicity adjusters" are those pharmaceutically acceptable inert substances that can be added to the formulation to provide an isotonicity of a composition. A typical tonicity adjuster in the formulation of the disclosure is an inorganic salt. Without being limiting, inorganic salts for adjusting the osmolality of the composition of the disclosure include NaCl, KCl, $CaCl_2$, and $MgCl_2$, in particular NaCl. The concentration of inorganic salt may range from 10 mM to 200 mM, 10 mM to 150 mM, 50 mM to 150 mM, 100 mM to 150 mM, or 100 mM to 120 mM. In a specific aspect, the concentration of salt (typically NaCl) which may be included in the formulations of the disclosure may be about 10 mM, about 25 mM, about 50 mM, about 75 mM, about 100 mM, about 110 mM, about 115 mM, about 130 mM, about 150 mM, or about 200 mM.

In some embodiments, instead of or in addition to acting as a tonicity adjuster, NaCl may help reduce irritation in the respiratory tract, e.g. reduce coughing, and/or further stabilize the present therapeutic proteins. In some embodiments, the concentration of NaCl in the present formulation ranges from about 100 mM to about 200 mM. Typically, 115 mM of NaCl is used.

The formulations of the present disclosure may further contain one or more surfactants, typically non-ionic surfactants. Protein solutions, in particular antibody solutions, have a high surface tension at the air-water interface. In order to reduce this surface tension, proteins, such as antibodies, tend to aggregate at the air-water interface. A surfactant minimizes antibody aggregation at the air-water interface, thereby helping to maintain the biological activity of the antibody in solution or during aerosolization. When the formulation is lyophilized, the surfactant may also reduce the formation of particulates in the reconstituted formulation.

Certain exemplary non-ionic surfactants include fatty alcohol, polysorbates such as polysorbate 20, polysorbate 80, Triton X-100, polyoxypropylene-polyoxyethylene copolymer (PLURONIC®), and nonyl phenoxypolyethoxyethanol (NP-40). Other surfactants which can be used in the formulation of the disclosure include phosphoglycerides, such as phosphatidyl cholines (lecithin), such as the naturally occurring surfactant, dipalmitoyl phosphatidyl choline (DPPC). Other exemplary surfactants include diphosphatidyl glycerol (DPPG), hexadecanol, polyoxyethylene-9-lauryl ether, a surface active fatty acid, such as palmitic acid or oleic acid, sorbitan trioleate (Span 85), glycocholate, surfactin, a poloxamer, a sorbitan fatty acid ester such as sorbitan trioleate, tyloxapol and a phospholipid.

The concentration of the surfactant may range from between 0.001% and 1% (v:v) (typically between 0.001% and 0.1% (v:v), or between 0.01% and 0.1% (v:v) such as about 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the formulation, typically from about 0.04% to 0.08% (v:v)). In a specific embodiment, the surfactant is polysorbate 20 or polysorbate 80, which is at a concentration of 0.001% (v:v), 0.005% (v:v), 0.01% (v:v), 0.02% (v:v), 0.04%, 0.05% (v:v), 0.08% (v:v), 0.1% (v:v), 0.5% (v:v) or 1% (v:v) of the formulation, typically 0.04% to 0.08% (v:v).

An example of a typical formulation of the disclosure comprises 0.01% (v:v) polysorbate 80, 0.02% (v:v) polysorbate 80, 0.05% (v:v) polysorbate 80 or 0.08% (v:v) polysorbate 80. Typically, polysorbate 80, 0.02% (v:v) is used.

Another example of a typical formulation of the disclosure comprises 0.01% (v:v) polysorbate 20, 0.02% (v:v) polysorbate 20, 0.05% (v:v) polysorbate 20 or 0.08% (v:v) polysorbate 20. More typically, polysorbate 20, 0.02% (v:v) is used.

The present therapeutic protein formulation can also comprise further pharmaceutically acceptable excipients, which serve to optimize the characteristics of the formulation and/or the characteristics of the aerosol. Examples of such excipients include taste-masking agents, sweeteners, and flavors.

The formulation of the disclosure is typically prepared by combining, in addition to the therapeutic proteins as described herein, an amino acid, such as histidine, wherein the histidine has a net charge at a pH between about 5.5 and 8, in an aqueous carrier or combining the therapeutic proteins as described herein with an aqueous carrier further comprising a histidine buffer. Further, NaCl, or optionally a surfactant, pH adjusting agents and additional excipients can be added as needed. Persons having ordinary skill in the art will understand that the combining of the various components to be included in the formulation can be done in any appropriate order. For example, the buffer can be added first, middle or last and the surfactant can also be added first, middle or last. It is also to be understood by one of ordinary skill in the art that some of these chemicals can be incompatible in certain combinations, and accordingly, are easily substituted with different chemicals that have similar properties but are compatible in the relevant mixture.

Therapeutic Proteins

In some embodiments, the one or more therapeutic proteins of the present formulation comprise an antibody for use in treating biofilm-associated disease(s) or disorder(s). As used herein "biofilm-associated disease(s) or disorder(s)" includes diseases or disorders which are characterized by the presence or potential presence of a biofilm, e.g., a bacterial biofilm. Biofilm-associated diseases or disorders include infection of the subject by one or more bacteria, e.g., *Pseudomonas aeruginosa, Bacillus subtilis, Candida albicans, Staphylococcus aureus, Staphylococcus epidermidis, Enterococcus faecalis, Helicobacter pylori, Escherichia coli, Salmonella typhimurium, Legionella pneumophila*, or other gram-negative or gram positive bacteria. Examples of biofilm-associated diseases or disorders include diseases or disorders caused by, for example, bacteria (e.g., gram-positive and/or gram-negative bacteria), fungi, viruses and parasites. Examples of biofilm-associated diseases or disorders include, but are not limited to, cystic fibrosis, middle ear infections including otitis media, osteomyelitis, acne, dental cavities or plaque and periodontitis, prostatitis, abscesses, bacteremia, contamination of peritoneal dialysis fluid, endocarditis, pneumonia, meningitis, pharyngitis, sinusitis, scarlet or rheumatic fever, urinary tract infection, laryngotracheitis, erysipeloid, gas gangrene, tetanus, typhoid fever, acute gastroenteritis, bronchitis, epiglottitis, plague, sepsis, chancroid, wound and burn infection, cholera, glanders, genital infections, empyema, granuloma inguinale, Legionnaire's disease, paratyphoid, bacillary dysentary, brucellosis, diphtheria, pertussis, toxic shock syndrome, mastitis, eye infections, including contact lens infections, catheter- or medical device-associated infections such as pacemaker leads. Other biofilm-associated diseases or disorders include swine erysipelas, peritonitis, encephalitis, anthrax, nocardiosis, pericarditis, mycetoma, peptic ulcer, melioidosis, Haverhill fever, tularemia, Moko disease, galls (such as crown, cane and leaf), hairy root, bacterial rot, bacterial blight, bacterial brown spot, bacterial wilt, bacterial fin rot, dropsy, columnaris disease, pasteurellosis, furunculosis, enteric redmouth disease, and vibriosis of fish.

Typically, the present antibodies are directed against DNABII proteins, such as integration host factor (IHF) and histone-like proteins (HU). Accordingly, in some embodiments the present formulations may comprise two or more therapeutic proteins comprising the antibodies described herein.

Methods for making monoclonal antibodies by hybridomas or other means and approaches are well known. See, for example, Niman et al, *Proc. Natl. Acad. Sci. USA*, 1983, 80:4949-4953, which is herein incorporated by reference in its entirety. Typically, a pathogen, pathogen protein, or a peptide analog is used either alone or conjugated to an immunogenic carrier, as the immunogen for producing monoclonal antibodies. The hybridomas are screened for the ability to produce an antibody that immunoreacts with the virus, protein or peptide analog.

Immunization is not necessarily required, however, as natural exposure to the pathogen may induce protective antibodies. More particularly, antibodies suitable for use in the present formulations and methods of the disclosure include those described in WO 2015/048484 and U.S. Pat. No. 10,233,234, each of which is herein incorporated by reference in its entirety. In some embodiments, the antibodies are anti-DNABII antibodies. For example, in some embodiments, the present formulation includes a therapeutic protein comprising a monoclonal antibody such as TRL1068, TRL1330, TRL1337, or a formulation comprising at least two anti-DNABII antibodies. In particular embodiments, the anti-DNABII antibody comprises TRL1068. For multiple antibody embodiments, targeting both DNABII and Type IV pilin proteins may provide advantages [Mokrzan E M, Ahearn C P, Buzzo J R, Novotny L A, Zhang Y, Goodman S D, Bakaletz L O. Nontypeable Haemophilus influenzae newly released (NRel) from biofilms by antibody-mediated dispersal versus antibody-mediated disruption are phenotypically distinct. *Biofilm.* 2:100039 (2020)]. In some embodiments, the present formulation comprises humanized or chimerized versions of the foregoing antibodies.

As is well known, the specificity of monoclonal antibodies is essentially determined by the complementarity-determining regions (CDRs) that are present in the variable regions of the light and heavy chains. Accordingly, in some embodiments, a therapeutic protein formulation is provided, which comprises a therapeutic protein comprising light and/or heavy chain CDRs and associated framework regions but without Fc region sequences, including single chain Fv, Fab, Fab', F(ab')2 constructs.

In some embodiments, the present therapeutic formulation comprises one or more anti-DNABII monoclonal antibodies comprising a heavy and a light chain, wherein the heavy chain comprises: (a1) the TRL1068 heavy chain CDR sequences HCDR1/HCDR2/HCDR3 (SEQ ID NO: 1). In other embodiments, the one or more anti-DNABII monoclonal antibodies binds to the same epitope as the antibody of (a1) and comprises a heavy and a light chain, wherein the heavy chain comprises: (a2) a polypeptide having at least 80%, such as at least 85%, such as at least 90%, such as at least 95%, such as at least 98%, or such as at least 99% sequence identity with the TRL1068 heavy chain CDR sequences HCDR1/HCDR2/HCDR3 (SEQ ID NO: 1).

In some embodiments, the present therapeutic formulation comprises one or more anti-DNABII monoclonal antibodies comprising a heavy and a light chain, wherein the heavy chain comprises: (b1) the TRL1330 heavy chain CDR sequences HCDR1/HCDR2/HCDR3 (SEQ ID NO: 2). In other embodiments, the one or more anti-DNABII monoclonal antibodies binds to the same epitope as the antibody of (b1) and comprises a heavy and a light chain, wherein the heavy chain comprises: (b2) a polypeptide having at least 80%, such as at least 85%, such as at least 90%, such as at least 95%, such as at least 98%, or such as at least 99% sequence identity with the TRL1330 heavy chain CDR sequences HCDR1/HCDR2/HCDR3 (SEQ ID NO: 2).

In some embodiments, the present therapeutic formulation comprises one or more anti-DNABII monoclonal antibodies comprising a heavy and a light chain, wherein the heavy chain comprises: (c1) the TRL1337 heavy chain CDR sequences HCDR1/HCDR2/HCDR3 (SEQ ID NO: 3). In other embodiments, the one or more anti-DNABII monoclonal antibodies binds to the same epitope as the antibody of (c1) and comprises a heavy and a light chain, wherein the heavy chain comprises: (c2) a polypeptide having at least 80%, such as at least 85%, such as at least 90%, such as at least 95%, such as at least 98%, or such as at least 99% sequence identity with the TRL1337 heavy chain CDR sequences HCDR1/HCDR2/HCDR3 (SEQ ID NO: 3).

In some embodiments, the present formulation includes at least two anti-DNABII monoclonal antibodies comprising a heavy and a light chain, wherein (i) the heavy chain of the first antibody comprises: the TRL1068 heavy chain CDR sequences HCDR1/HCDR2/HCDR3 (SEQ ID NO: 1);

(ii) the heavy chain of the second antibody comprises: the TRL1330 heavy chain CDR sequences HCDR1/HCDR2/HCDR3 (SEQ ID NO: 2); or (iii) the heavy chain of the second antibody comprises: the TRL1337 heavy chain CDR sequences HCDR1/HCDR2/HCDR3 (SEQ ID NO: 3.

In some embodiments, the monoclonal antibodies in the present formulation are all of the same IgG subtype and have identical or near identical constant region sequences. In a particular aspect, all antibodies in the combination are IgG1 antibodies. In some embodiments, the antibodies are typically designed and expressed with similar or comparable constant region sequences and are typically of the same IgG, selected from human IgG1, IgG2, IgG2, IgG3, or IgG4. Modified Fc sequences to provide longer half-life in circulation are also known in the art.

In some embodiments, the present antibodies comprise human heavy and light chain constant regions as are known in the art. In some embodiments, the present anti-DNABII antibodies comprise a human IgG1 constant region amino acid sequence. In some embodiments, anti-DNABII antibodies are provided comprising a human IgG1 constant region amino acid sequence. In some embodiments, the present anti-DNABII antibodies comprise a human light chain kappa constant region or a human light chain lambda constant region.

In some embodiments, the present therapeutic formulation comprises one or more anti-DNABII monoclonal antibodies comprising a heavy and a light chain, wherein the heavy chain comprises: (a1) the heavy chain amino acid sequence of TRL1068 (SEQ ID NO: 1). In other embodiments, the one or more anti-DNABII monoclonal antibodies binds to the same epitope as the antibody of (a1) and comprises a heavy and a light chain, wherein the heavy chain comprises: (a2) a polypeptide having at least 80%, such as at least 85%, such as at least 90%, such as at least 95%, such as at least 98%, or such as at least 99% sequence identity with the amino acid sequence of TRL1068 (SEQ ID NO: 1). In certain embodiments of (a2), any amino acid substitutions, additions, or deletions in the heavy chain amino acid sequence of TRL1068 (SEQ ID NO: 1) are located in the framework regions. In certain embodiments of (a2), the CDRs differ by no more than 5, 4, 3, 2, or 1 amino acid residue(s) relative to the CDRs in the heavy chain amino acid sequence of TRL1068 (SEQ ID NO: 1).

In addition or alternatively to (a1) and/or (a2), the present therapeutic formulation comprises one or more anti-DNABII monoclonal antibodies comprising a heavy and a light chain, wherein the heavy chain comprises: (b1) the heavy chain amino acid sequence of TRL1330 (SEQ ID NO: 2) and/or the one or more anti-DNABII monoclonal antibodies comprises an antibody that binds to the same epitope as the antibody of (b1) comprising a heavy and a light chain, wherein the heavy chain comprises: (b2) a polypeptide having at least 80%, such as at least 85%, such as at least 90%, such as at least 95%, such as at least 98%, or such as at least 99% sequence identity with the heavy chain amino acid sequence of TRL1330 (SEQ ID NO: 2). In certain embodiments of (b2), any amino acid substitutions, additions, or deletions in the heavy chain amino acid sequence of TRL1330 (SEQ ID NO: 2) are located in the framework regions. In certain embodiments of (b2), the CDRs differ by no more than 5, 4, 3, 2, or 1 amino acid residue(s) relative to the CDRs in the heavy chain amino acid sequence of TRL1330 (SEQ ID NO: 2).

In addition or alternatively to (a1), (a2), (b1) or (b2), the present therapeutic formulation comprises one or more anti-DNABII monoclonal antibodies comprising a heavy and a light chain, wherein the heavy chain comprises: (c1) a heavy chain amino acid sequence of TRL1337 (SEQ ID NO: 3); and/or wherein the one or more anti-DNABII monoclonal antibodies comprises an antibody that binds to the same epitope as the antibody of (c1) comprising a heavy and a light chain, wherein the heavy chain comprises: (c2) a polypeptide having at least 80%, such as at least 85%, such as at least 90%, such as at least 95%, such as at least 98%, or such as at least 99% sequence identity with the heavy chain amino acid sequence of TRL1337 (SEQ ID NO: 3). In certain embodiments of (c2), any amino acid substitutions, additions, or deletions in the heavy chain amino acid sequence of TRL1337 (SEQ ID NO: 3) are located in the framework regions. In certain embodiments of (c2), the CDRs differ by no more than 5, 4, 3, 2, or 1 amino acid residue(s) relative to the CDRs in the heavy chain amino acid sequence of TRL1337 (SEQ ID NO: 3).

The present formulation may include at least two anti-DNABII monoclonal antibodies comprising a heavy and a light chain, wherein
(i) the heavy chain of the first antibody comprises: the heavy chain amino acid sequence of TRL1068 (SEQ ID NO: 1);
(ii) the heavy chain of the second antibody comprises: the heavy chain amino acid sequence of TRL1330 (SEQ ID NO: 2); or
(iii) the heavy chain of the second antibody comprises the heavy chain amino acid sequence of TRL1337 (SEQ ID NO: 3).

In some embodiments, the present therapeutic formulation comprises one or more anti-DNABII monoclonal antibodies comprising a heavy and a light chain, wherein the heavy and the light chain comprise: (a1) a heavy chain amino acid sequence of TRL1068 (SEQ ID NO: 1) and a light chain amino acid sequence of TRL1068 (SEQ ID NO: 4); and/or wherein the one or more anti-DNABII monoclonal antibodies comprises an antibody that binds to the same epitope as the antibody of (a1) comprising a heavy and a light chain, wherein the heavy chain and the light chain comprise: (a2) a polypeptide having at least 80%, such as at least 85%, such as at least 90%, such as at least 95%, such as at least 98%, or such as at least 99% sequence identity with the heavy chain amino acid sequence of TRL1068 (SEQ ID NO: 1) and the light chain amino acid sequence of TRL1068 (SEQ ID NO: 4). In certain embodiments of (a2), any amino acid substitutions, additions, or deletions in the heavy chain and light chain amino acid sequences of TRL1068 (SEQ ID NO: 1 and SEQ ID NO: 4, respectively) are located in the framework regions. In certain embodiments of (a2), the CDRs differ by no more than 5, 4, 3, 2, or 1 amino acid residue(s) relative to the CDRs in the heavy chain and light chain amino acid sequences of TRL1068 (SEQ ID NO: 1 and SEQ ID NO: 4, respectively).

In addition or alternatively to (a1) and/or (a2), the present therapeutic formulation comprises one or more anti-DNABII monoclonal antibodies comprising a heavy and a light chain, wherein the heavy and the light chain comprise: (b1) a heavy chain amino acid sequence of TRL1330 (SEQ ID NO: 2) and a light chain amino acid sequence of TRL1330 (SEQ ID NO: 5) and/or wherein the one or more anti-DNABII monoclonal antibodies comprises an antibody that binds to the same epitope as the antibody of (b1) comprising a heavy and a light chain, wherein the heavy and light chain comprise: (b2) a polypeptide having at least 80%, such as at least 85%, such as at least 90%, such as at least 95%, such as at least 98%, or such as at least 99% sequence identity with the heavy chain amino acid sequence of TRL1330 (SEQ ID NO: 2) and the light chain amino acid sequence of TRL1330 (SEQ ID NO: 5). In certain embodiments of (b2), any amino acid substitutions, additions, or deletions in the heavy chain and light chain amino acid sequences of TRL1330 (SEQ ID NO: 2 and SEQ ID NO: 5, respectively) are located in the framework regions. In certain embodiments of (b2), the CDRs differ by no more than 5, 4, 3, 2, or 1 amino acid residue(s) relative to the CDRs in the heavy chain and light chain amino acid sequences of TRL1330 (SEQ ID NO: 2 and SEQ ID NO: 5, respectively).

In addition or alternatively to (a1), (a2), (b1) or (b2), the present therapeutic formulation comprises one or more anti-DNABII monoclonal antibodies comprising a heavy and light chain, wherein the heavy and the light chain comprise: (c1) a heavy chain amino acid sequence of TRL1330 (SEQ ID NO: 3) and a light chain amino acid sequence of TRL1337 (SEQ ID NO: 6) and/or wherein the one or more anti-DNABII monoclonal antibodies comprises an antibody that binds to the same epitope as the antibody of (c1) comprising a heavy and a light chain, wherein the heavy and light chain comprise: (c2) a polypeptide having at least 80%, such as at least 85%, such as at least 90%, such as at least 95%, such as at least 98%, or such as at least 99% sequence identity with the heavy chain amino acid sequence of TRL1337 (SEQ ID NO: 3) and the light chain amino acid sequence of TRL1337 (SEQ ID NO: 6). In certain embodiments of (c2), any amino acid substitutions, additions, or deletions in the heavy chain and light chain amino acid sequences of TRL1337 (SEQ ID NO: 3 and SEQ ID NO: 6, respectively) are located in the framework regions. In certain embodiments of (c2), the CDRs differ by no more than 5, 4, 3, 2, or 1 amino acid residue(s) relative to the CDRs in the heavy chain and light chain amino acid sequences of TRL1337 (SEQ ID NO: 3 and SEQ ID NO: 6, respectively).

Typically, the present formulation includes at least three anti-DNABII monoclonal antibodies comprising a heavy and a light chain, wherein
(i) the heavy and the light chain of the first antibody comprises, respectively: the heavy chain amino acid sequence of TRL1068 (SEQ ID NO: 1) and the light chain amino acid sequence of TRL1068 (SEQ ID NO: 4);
(ii) the heavy and the light chain of the second antibody comprises, respectively: the heavy chain amino acid sequence of TRL1330 (SEQ ID NO: 2) and the light chain amino acid sequence of TRL1330 (SEQ ID NO: 5); and
(iii) the heavy and light chain of the third antibody comprise: the heavy chain amino acid sequence of TRL1337 (SEQ ID NO: 3) and the light chain amino acid sequence of TRL1337 (SEQ ID NO: 6).

In some embodiments, the present antibodies exhibit the following binding affinity (KD) for DNABII proteins derived therefrom, such as recombinant IHF proteins: between about $5\times10^{-8}$ M and about $5\times10^{-12}$ M, such as about $5\times10^{-9}$ M to about $5\times10^{-11}$ M, such as about $3\times10^{-9}$ M to about $3\times10^{-11}$ M. In some embodiments, the binding affinity is about $5\times10^{-19}$ M to about $5\times10^{-11}$ M. In some embodiments, the present antibodies exhibit a KD of less than 10 nM, less than 3 nM, or less than 1 nM for recombinant DNABII protein. In some embodiments, the present antibodies exhibit KDs of between 10 nM and 0.1 pM. In some embodiments, the present antibodies exhibit KDs of between 3 nM and 1 pM.

As used herein, "binding affinity" in reference to antibodies refers to the KD (the equilibrium dissociation constant between the antibody and its antigen), which can be determined by various methods known in the art. For example, the KD may be measured by determining oblique-incidence reflectivity difference (OI-RD) by use of a microarray or fluidic system, e.g., by ABCAM®. See Landry et al., 2012, *Assay and Drug Dev. Technol.* 10: 250-259, which is herein incorporated by reference in its entirety, BIACORE® (i.e., surface plasmon resonance) or competitive binding assays.

In some embodiments, the antibodies of the present formulation lack the Fc and/or have reduced complement mediated effector function. WO 2015/120097, which is herein incorporated by reference in its entirety, demonstrates that Fc function and Fc portions of neutralizing antibodies, are not necessarily required for enhanced efficacy after intranasal and/or inhalation administration. Thus, antibody fragments, such as Fab fragments, or antibodies lacking Fc or lacking effector function, are effective intranasally or upon inhalation administration. In some embodiments, the antibodies of the present formulation may be selected from Fab, Fab', and F(ab')2. Data indicating that the mechanism of action of antibodies to DNABII proteins is not complement dependent is provided in [Brockson M E, Novotny L A, Mokrzan E M, Malhotra S, Jurcisek J A, Akbar R, Devaraj A, Goodman S D, Bakaletz L O. Evaluation of the kinetics and mechanism of action of anti-integration host factor-mediated disruption of bacterial biofilms. *Mol Microbiol.* 93 (6):1246-58 (2014).].

The present antibodies may be derived from a recombinant protein, may be recombinantly expressed or may be derived or generated by other means or methods, including means or methods to provide neutralizing antibody within the respiratory tract, including by way of genetic material or DNA or DNA vector expression, such as by delivering DNA or RNA encoding anti-DNABII antibody or fragment(s) thereof.

In some embodiments, the therapeutic proteins of the present formulation comprise a combination of two, three, four, five, six, seven, eight, nine, ten, or more antibodies thereof in any ratio. In some embodiments, the therapeutic proteins of the present formulation comprise from 2-10 or 3-5 antibodies on a per weight basis of approximately 10-80 wt %; 20-50 wt %; 25-40 wt %, of each antibody per total antibody weight in the composition. In a specific embodiment, the therapeutic proteins of the present formulation comprise a substantially equal dose or ratio of a first, second and third antibody at approximately 33 wt %±3 wt % of each of first, second and third antibodies per total wt of antibody in the formulation.

In some embodiments, the therapeutic proteins of the present formulation comprise from 2-10 antibodies in a single dose, wherein a therapeutically effective amount of each antibody in the combination may be of less than 10 mg/kg body weight, of less than 5 mg/kg body weight, of less than 2 mg/kg body weight, of I mg/kg body weight or less. The single dose amount of each antibody in the combination may be of less than I mg/kg body weight, of less than 0.5 mg/kg, of less than 0.I mg/kg, of less than 0.05 mg/kg. Multiple doses of the antibody combination may be administered. Each combination dose may be the same or the doses may differ, such as an initial higher dose, followed by lower doses, or an initial lower dose, followed by higher doses. The single dose or doses or any dose may be of less than I mg/kg body weight, of less than 0.5 mg/kg, of less than 0.I mg/kg, of less than 0.05 mg/kg. The initial dose may be greater than 1 mg/kg and further or subsequent doses may be lower or may be less than 1 mg/kg.

In some embodiments, a dose of each antibody in the formulation that is intended for respiratory tract administration, particularly intranasal administration or inhalation administration, is in an amount less than 1 mg/kg on the basis of the body weight of a mammal. In some embodiments, formulations are provided comprising antibody amounting to administration of less than 10 mg/kg, less than 5 mg/kg, or less than 1 mg/kg on the basis of the body weight of a human. Formulations of the present disclosure may particularly comprise a dose of antibody that is intended for administration, particularly intranasally or via inhalation, in an amount less than 1 mg/kg, less than 0.5 mg/kg, less than 0.1 mg/kg, less than 0.05 mg/kg, less than 0.01 mg/kg, less than 0.005 mg/kg, less than 0.0025 mg/kg, less than 0.001 mg/kg on the basis of the body weight of a mammal, including a clinically relevant mammal, such as a mouse, dog, horse, cat or a human. In some embodiments, a therapeutically effective dose is selected from about 100 mg/kg, 50 mg/kg, 10 mg/kg, 3 mg/kg, 1 mg/kg, or 1 mg/kg. In some aspects, an effective prophylactic dose or post-exposure prophylactic dose is selected from about 1 mg/kg/ 0.1 mg/kg or about 0.01 mg/kg.

One of skill in the art can determine, including on the basis of efficacy in animal models and in consideration of clinical and physiological response, the appropriate and efficacious dose in a mammal, including a human. Thus, the disclosure and dosing parameters are not limited by the disclosure.

Aerosolization

In some embodiments, the present formulation produces liquid particles upon aerosolization. Aerosolization is the process of forming an aerosol. As used herein "an aerosol" comprises a continuous gas phase and, dispersed therein, a discontinuous or dispersed phase of liquid particles or droplets. The liquid particles or droplets of the dispersed phase comprise the therapeutic protein of the present formulation in a liquid environment. The liquid environment is mainly an aqueous phase with the further excipients as described herein. The continuous gas phase of the aerosol may be selected from any gas or mixture of gases. Typically, the gas or mixture is pharmaceutically acceptable. For example, the gas may be air or compressed air. Alternatively, other gases and gas mixtures, such as air enriched with oxygen, carbon dioxide, or mixtures of nitrogen and oxygen may be used. Typically, the gas is air or compressed air.

In some embodiments, a membrane (or mesh) nebulizer is used to generate the aerosol of the disclosure. A "nebulizer" as defined herein is a device which is capable of aerosolizing a liquid material into a dispersed liquid phase.

In some embodiments, the present liquid formulation is nebulized by vibrating the present formulation. Such an oscillating fluid membrane nebulizer comprises a reservoir in which a liquid to be nebulized is filled. When operating the nebulizer, the liquid is fed to a membrane via a liquid feed system that is made to oscillate (i.e. vibrate, e.g. by means of a piezoelectric element). In some embodiments, such liquid feed system includes vibrating a back wall of the reservoir (e.g. AEROVECTRX™ Technology, Pfeifer Technology) or vibrating a liquid transporting slider (e.g. I-NEB™ device from Respironics, or U22™ device from Omron). Such nebulizers are referred to herein as "passive membrane nebulizers".

In other embodiments, the present formulation is nebulized by vibrating the membrane ("vibrating mesh nebulizer"). Nebulizers of this type comprise a reservoir that is filled with the liquid to be nebulized. When operating the nebulizer, a liquid, e.g., the formulation of the present disclosure, is fed to a membrane that is made to oscillate, i.e. vibrate (e.g. by means of a piezoelectric element). The liquid present at one side of the vibrating membrane is transported through openings in the vibrating membrane (also referred to as "pores" or "holes") and takes the form of an aerosol on the other side of the vibrating membrane. (e.g. EFLOW™ rapid and ERAPID™ from PARI, HL100 from Health and Life as well as AEROGEN® Go and AEROGEN® Solo Ultrasonic Nebulizer (Aerogen, Inc., Ireland). Such nebulizers are referred to herein as "active membrane nebulizers."

Different membrane types are available for the nebulization of liquids with a membrane nebulizer. These membranes are characterized by different pore sizes, which generate aerosols with different particle sizes. Depending on the desired aerosol characteristics, different membrane types (i.e. different modified membrane nebulizers or aerosol generators) can be used.

Two values can be determined experimentally and used to describe the particle size of the generated aerosol: the mass median diameter (MMD) and the mass median aerodynamic diameter (MMAD). The difference between the two values is that the MMAD is normalized to the density of water. The MMAD may be measured by an impactor, for example the Anderson Cascade Impactor (ACI) or the Next Generation Impactor (NGI). Alternatively, laser diffraction methods may be used, for example the MALVERN MASTERSIZER X™, to measure the MMD.

Another parameter describing the dispersed phase of the aerosol is the particle size distribution of the aerosolized liquid particles. The geometric standard deviation (GSD) is an often used measure for the broadness of the particle or droplet size distribution of generated aerosol particles or droplets.

For aerosol delivery into the respiratory tract, the particles include an MMAD ranging from 1 μm to 11 μm, such as 1.5 μm to 5 μm, such as 2.3 μm to 4.5 μm. In some embodiments, the MMAD is below 10.0 μm, such as below 5.0 μm, such as below 3.3 μm or such as below 2.3 μm. In some embodiments, the size distribution has a GSD ranging from 1 to 3, such as from 1.5 to 2.5, such as from 1.8 to 2.3. In some embodiments, the size distribution has a GSD of less than 2.3, typically less than 2.0, more typically less than 1.8 or even more typically less than 1.6. Such particle size distribution is particularly useful to achieve a high local therapeutic protein concentration in the respiratory tract of humans, relative to the amount of therapeutic protein which is aerosolized.

The selection of a precise particle size of the foregoing particle size ranges should take the target region or tissue for deposition of the aerosol into account. For example, the optimal droplet diameter will differ depending on whether nasal or oral inhalation is intended, and whether upper (e.g., nostrils, nasal cavity, mouth, throat (pharynx), and voice box (larynx) and/or lower respiratory tract delivery (e.g. trachea, lungs, bronchi, alveoli) is focused upon. Additionally, the age-dependent anatomic geometry (e.g. the nose, mouth or respiratory airway geometry) as well as the respiratory disease and condition of the patients and their breathing pattern belong to the factors determining the optimal particle size (e.g. MMAD) for therapeutic protein delivery to the lower or upper respiratory tract.

In some embodiments, the aerosol is for upper respiratory tract delivery, in particular, the nose, nasal and/or sinonasal mucosa, osteomeatal complex, and paranasal cavities. In these embodiments, the MMAD ranges from about 1 μm to about 10 μm, such as about 3 μm to about 10 μm, such as about 3 μm to about 5 μm. In some embodiments the MMAD is below about 10 μm, such as below about 5.0 μm, or such as below about 4.5 μm, or such as below about 4.0 μm, or such as below about 3.3 or such as below about 3.0 μm is particularly suitable.

In some embodiments, the formulation is for lower respiratory tract delivery, in particular, deep into the lungs.

Generally, small airways, which are defined by an internal diameter typically lower than 2 mm, represent almost 99% of the lung volume and therefore play a large role in lung function. Alveoli are sites in the deep lungs where oxygen and carbon dioxide are exchanged with the blood. Inflammation in the alveoli induced by some viruses or bacteria leads to fluid secretion on site and directly affects oxygen uptake by the lungs. Therapeutic targeting of deep pulmonary airways with aerosols typically includes particles having an MMAD ranging from about 1 μm to about 5 μm, such as about 2 μm to about 4 μm, such as about 3 μm to about 5 μm. In some embodiments, the MMAD is below 5.0 μm, typically below 4.5 μm, such as 4.0 μm, more typically below 3.3 μm and even more typically below 3.0 μm.

In some embodiments, the aerosol is to be deposited into the lungs of children and/or infants. In these embodiments, smaller droplet sizes (MMADs) are used, ranging from e.g., about 1.0 to about 3.3 μm, more typically below 2.0 μm.

In aerosol therapy, the fraction of particles smaller than a certain size, e.g., an MMAD smaller than 5 μm (representing the fraction typically respirable by an adult), or 3.3 μm (representing the fraction typically respirable by a child or which is typically deposited in the deeper lungs of an adult) may be evaluated. Also, the fraction of particles smaller than 2 μm is often evaluated as it represents the fraction of the aerosol that could optimally reach terminal bronchioles and alveoli of adults and children and can penetrate the lungs of infants and babies.

In the some embodiments, the fraction of droplets having a particle size smaller than 5 μm is typically greater than 40%, is typically greater than 65%, more typically greater than 70% and even more typically greater than 80%. The fraction of droplets having a particle size smaller than 3.3 μm is typically greater than 25%, more typically greater than 30%, even more typically greater than 35% and still more typically greater than 40%. The fraction of droplets having a particle size smaller than 2 μm is typically greater than 4%, more typically greater than 6% and even more typically greater than 8%.

A typical membrane nebulizer for targeting the upper respiratory tract is a nebulizer which generates the aerosol via a perforated vibrating membrane principle, such as a modified investigational membrane nebulizer using the EFLOW™ technology, but which is also capable of emitting a pulsating air flow so that the generated aerosol cloud pulsates (i.e. undergoes fluctuations in pressure) at the desired location or during transporting the aerosol cloud to the desired location (e.g. sinonasal or paranasal sinuses). This type of nebulizer has a nose piece for directing the flow transporting the aerosol cloud into the nose. Aerosols delivered by such a modified electronic nebulizer may reach sinonasal or paranasal cavities much better than when the aerosol is delivered in a continuous (non-pulsating) mode. The pulsating pressure waves may achieve a more intensive ventilation of the sinuses so that a concomitantly applied aerosol is better distributed and deposited in these cavities. More particularly, a typical nebulizer for targeting the upper respiratory tract of a subject is a nebulizer adapted for generating an aerosol at an effective flow rate of less than about 5 liters minute and for simultaneously operating means for effecting a pressure pulsation of the aerosol at a frequency in the range from about 10 to about 90 Hz, wherein the effective flow rate is the flow rate of the aerosol as it enters the respiratory system of the subject. Examples of such electronic nebulization devices are disclosed in WO 2009/027095, which is herein incorporated by reference in its entirety.

In a typical embodiment of the disclosure, the nebulizer for targeting the upper respiratory tract is a nebulizer which uses a transportation flow that can be interrupted when the aerosol cloud reaches the desired location and then starts the pulsation of the aerosol cloud, e.g., in an alternating mode, such as described in WO 2011/134940, which are each herein incorporated by reference in its entirety. For aerosol delivery to the nose, e.g., the SINUS™ device (jet nebulizer) from PARI and also a membrane nebulizer (prototypes of VIBRENT™ technology) may be used. The suitability of the generated aerosol for application to the upper airways can be evaluated in nasal inhalation models such as the human nasal cast model described in WO 2009/027095, which is herein incorporated by reference in its entirety.

If the method is intended for targeting the lower respiratory tract such as the bronchi or the deep lungs, a piezoelectric perforated membrane-type nebulizer is typically selected for generating the aerosol. Examples of suitable nebulizers include the passive membrane nebulizer, such as I-NEB™, U22™, U 1™, MICRO AIR™, the ultrasonic nebulizer, for example MULTISONIC™, and/or an active membrane nebulizer, such as HL1 00™, RESPIMATE™, EFLOW™ Technology nebulizers, AEROGEN® Solo Ultrasonic Nebulizer, AERONEB PRO™, AEROGEN® GO, and AEROGEN® DOSE device families as well as the Pfeifer, Chrysalis (Philip Morris) or AEROVECTRX™ devices or the EFLOW™ nebulizer (electronic vibrating membrane nebulizer available from PARI, Germany). Alternatively a passive membrane nebulizer may be used, for example U22™ or U 1™ from Omron or a nebulizer based on the Telemaq.fr technique or the Ing. Erich Pfeiffer GmbH technique.

Whether adapted for pulmonary or sinonasal delivery, the nebulizer should typically be selected or adapted to be capable of aerosolizing a unit dose at a typical output rate. A unit dose is defined herein as a volume of the present aqueous therapeutic composition comprising the therapeutically effective amount of active compound, i.e. the therapeutic protein as described herein, designated to be administered during a single administration. In some embodiments, the nebulizer can deliver such a unit dose at a rate of at least 0.1 mL/minute or at a rate of at least 50 mg/minute.

The volume of the composition that is nebulized is typically low, which helps to reduce nebulization times. The volume, also referred to as the volume of a dose, or a dose unit volume, or a unit dose volume, should be understood as the volume, which is intended for being used for one single administration or nebulizer therapy session. Specifically, the volume may be in the range from 0.3 mL to 9.0 mL, typically 0.5 mL to 6 mL, or more typically 1.0 mL to about 4.5 mL, or even more typically about 3 mL. Typically, a nebulizer, as described herein, generates an aerosol where a major fraction of the loaded dose of liquid aqueous formulation is delivered as aerosol, i.e. to have a high output. More specifically, the nebulizer generates an aerosol which contains at least 50% of the dose of therapeutic protein in the formulation, or, in other words, which emits at least 50% of the liquid aqueous formulation filled in the reservoir.

Methods

In some embodiments, the present disclosure provides a method of generating an aerosol comprising the step of nebulizing the present therapeutic formulation, as described herein, using a nebulizer, as also herein described, to obtain an aerosol. Typically, the nebulizer is a vibrating mesh nebulizer as described herein.

In some embodiments, the present disclosure provides a method for the therapeutic and/or prophylactic treatment of biofilm-associated diseases or disorders, such as cystic fibrosis, ventilator-associated pneumonia, and acute exacerbations of chronic bronchitis or COPD, as herein described, which method comprises administering a therapeutically effective amount of the present therapeutic formulation, as also herein described, to a subject in need thereof. In some embodiments, the present therapeutic formulation is administered intranasally. In other embodiments, the therapeutic protein formulation of the present disclosure is administered by inhalation as described herein. Typically, the administration comprises inhaling an aerosol generated by a nebulizer, as also described herein, typically a vibrating membrane nebulizer. In some embodiments, the nebulizer generates an aerosol targeting the upper respiratory tract of a subject as herein described. Alternatively, the nebulizer generates an aerosol targeting the lower respiratory tract of a subject as described herein.

Therapeutic Adjunctive Therapy: mAb Binding to DNABII and Antibiotic

The second member of the combination therapy can be an antibiotic. For example, the antibiotic can be bacteriostatic or bactericidal against Gram positive or Gram negative target bacteria. Usually, where the bacteria are Gram negative, it can be preferred that the antibiotic is selected from carbapenems, polymyxins, carboxypenicillins, fluoroquinolones, aminoglycosides such as tobramycin, neomycin and gentamycin, and the like, and may include antimicrobial peptide. In many cases, the antibiotic is a macrolide, a minocycline, an amikacin, a gentamicin, a kanamycin, a neomycin, a netilmicin, a tobramycin, a paromomycin, a rifaximin, a cephalosporin, an aztreonam, a bacitracin, a sulfonamide, a tetracycline, antimicrobial peptide or the like. Bacteriostatic antibiotics may include without limitation a macrolide, minocycline, an amikacin, a gentamicin, a kanamycin, a neomycin, a netilmicin, a tobramycin, a paromomycin, a rifaximin, a cephalosporin, an aztreonam, a bacitracin, a sulfonamide, a tetracycline, and/or the like. For example, preferred antibiotics, from across a wide range of antibiotic families for combination with antibodies, can include ciprofloxacin, colistin, piperacillin, cefepime, tobramycin, meropenem, aztreonam, and/or the like.

The term bacteriostatic, as used herein, refers to antibiotics that stop growth of the target bacteria. Bacteriostatic antibiotics typically inhibit the growth and multiplication of the target bacteria. For example, a bacteriostatic antibiotic may target bacterial ribosomes, thus blocking translation of proteins and stopping growth. Bacteriostatic antibiotics can include, e.g., sulfonamides, macrolides, ethambutol, linezolid, tetracyclines, lincosamides, sulfamethoxazole, chloramphenicol, fusidic acid, trimethoprim, clindamycin, erythromycin, other members of the antibiotic families comprising these antibiotics, and/or the like. In certain embodiments, a bactericidal antibiotic, employed at a minimum inhibitory concentration (MIC) can also function as a bacteriostatic antibiotic in the context of the antibody combinations described herein. In preferred embodiments, the antibody/antibiotic combinations of the invention can comprise bacteriostatic and/or MIC levels of tobramycin, meropenem, ciproflaxin, colistin, piperacillin, cefepim, aztreonam, and/or the like.

Antibiotics are often described as bactericidal or bacteriostatic, though there is not necessarily a fine line between these effects. Bacteriostatic antibiotics are said to essentially stop the bacteria from metabolizing or multiplying (e.g., blocking transcription of peptides). Of course, this can ultimately lead to the death of the bacteria. Bacteriostatic antibiotics typically interfere with DNA replication of protein translation. Bactericidal antibiotics typically interfere with construction or integrity of a cell feature, such as the cell wall, destroying viability of the cell.

Antibiotics useful in combination with the antibodies of the present invention may include, e.g., bactericidal or bacteriostatic antibiotics. For example, the antibiotics can be aminoglycosides (e.g., gentamicin, amikacin, neomycin, tobramycin), quinolones (e.g., ciprofloxacin, levofloxacin), cephalosporins (e.g., ceftazidime, cefepime, cefoperazone, cefpirome, ceftobiprole), antipseudomonal penicillins, carboxypenicillins (e.g., carbenicillin and ticarcillin), ureidopenicillins (e.g., mezlocillin, azlocillin, and piperacillin), carbapenems (e.g., meropenem, imipenem, doripenem), polymyxins (e.g., polymyxin B and colistin), monobactams (e.g., aztreonam), or antimicrobial peptides (AMP).

β-lactam antibiotics (beta-lactam antibiotics) are antibiotics that contain a beta-lactam ring in their molecular structure. This includes penicillin derivatives (penams), cephalosporins and cephamycins (cephems), monobactams such as aztreonam, carbapenems and carbacephems. Most β-lactam antibiotics work by inhibiting cell wall biosynthesis in the bacterial organism and are the most widely used group of antibiotics.

In the specific case of certain bacteria there may be various levels of resistance to antibiotics. For example, Pseudomonas is often resistant to elimination by certain antibiotics (such as, e.g., kanamycin, moxifloxacin, cefuroxime, cefotaxime, ceftriaxone, ertapenem, and many penicillins), but these antibiotics may still surprisingly complement antibodies against the bacteria.

Antimicrobial peptides (AMPs), also called host defense peptides (HDPs) or innate immune peptides are part of the innate immune response. These peptides are potent, broad spectrum antibiotics. Antimicrobial peptides have been demonstrated to kill Gram negative and Gram positive bacteria, enveloped viruses, fungi and even cancerous cells. It appears that AMPs frequently destabilize biological membranes, can form transmembrane channels, and may also have the ability to enhance immunity by functioning as immunomodulators. In terms of antimicrobial action, AMPs may attack bacteria via both membrane and non-membrane mechanisms.

Although AMPs possess diverse structures, a majority of such peptides are short (less than 60 amino acids), cationic (on average +3) and amphipathic, allowing them to rapidly eliminate pathogens by targeting anionic membranes. Some AMPs display their antimicrobial activity via inhibiting cell wall synthesis of Gram-positive bacteria. Human β-defensin 3 (hBD3) and some bacterial antibiotics are such peptides. hBD3 is a highly charged host defense peptide (+11), which has a higher antimicrobial activity than hBD1 or hBD2.

AMPs can interact with non-membrane targets such as bacterial cell receptors or intracellular molecules. Many bacteriocins (bacterial AMPs) are thought to kill pathogens by a receptor-mediated mechanism.

The antimicrobial peptide database provides a useful tool for searching, predicting, and designing new AMPs. During 2015-2019, ~500 new natural peptides have been registered. Examples of AMPs include teixobactin, which is a cell wall inhibiting peptide antibiotic. Darobactin inhibits a chaperone and translocator for outer membrane proteins. cOB1, a sex pheromone from commensal enterococci, restricts the growth of multidrug-resistant *Enterococcus faecalis* in the gut at a picomolar concentration. A shrimp peptide MjPen-II comprises three different sequence domains: serine-rich, proline-rich, and cysteine-rich regions. Amphibian peptide urumin specifically inhibits H1 hemagglutinin-bearing influenza A virus. Defensins are abundant and typically consist of three pairs of intramolecular disulfide bonds. However, rat rattusin dimerizes via forming five pairs of intermolecular disulfide bonds. For a listing of available AMP, the Antimicrobial Peptide Database can be consulted. There are at least 3167 AMPs in the database, and are mainly natural peptides. See [Dang X, Wang G. Spotlight on the Selected New Antimicrobial Innate Immune Peptides Discovered During 2015-2019. *Curr Top Med Chem.* 20 (32):2984-2998 (2020)], contents of which are incorporated by reference in its entirety for the disclosure of the listing and discussion of various AMPs.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds).

EXAMPLES

The present invention is described in further detailed in the following examples which are not in any way intended to limit the scope of the invention as claimed. The attached Figures are meant to be considered as integral parts of the specification and description of the invention. All references cited herein are specifically incorporated by reference for all that is described therein. The following examples are offered to illustrate, but not to limit the claimed invention.

Example 1

Aerosol Characteristics

Three different formulations (formulations 1, 2 and 3) having the components shown in Table 1, below, each at a pH of 6.5, are prepared and assessed for their ability to generate particles after aerosolization and for retention of activity. As indicated in Table 1, all of the formulations contain one of three different antibodies (TRL1068, TRL1330 and TRL1337 (20 mg/mL)), 20 mM histidine-chloride buffer and 115 mM NaCL. Formulations 2 and 3, unlike formulation 1, however, additionally contains polysorbate-20 in an amount of 0.02% (v/v) or 0.05% (v/v), respectively.

TABLE 1

| Formulations with different amounts of polysorbate-20 | | | |
|---|---|---|---|
| Component | Formulation 1 (amount of component) | Formulation 2 (amount of component) | Formulation 3 (amount of component) |
| Antibody/Antibodies | 20 mg/mL total antibody | 20 mg/mL total antibody | 20 mg/mL total antibody |
| Histidine-chloride buffer | 20 mM | 20 mM | 20 mM |

29

TABLE 1-continued

Formulations with different amounts of polysorbate-20

| Component | Formulation 1 (amount of component) | Formulation 2 (amount of component) | Formulation 3 (amount of component) |
|---|---|---|---|
| NaCl | 115 mM | 115 mM | 115 mM |
| Polysorbate-20 | N/A | 0.02% (v/v) | 0.05% (v/v) |

Samples are subjected to ELISA to determine DNABII-binding ability for each of the antibodies (TRL1068, TRL1330 and TRL1337) in the formulations. Aerosolization is then performed using a nebulizer (AEROGEN® Solo Ultrasonic Nebulizer, Aerogen, Inc., Ireland). Two samples from each formulation are again subjected to ELISA to determine the DNABII-binding ability of each of the antibodies after nebulization.

After aerosolization, the aerosol particles are collected at a flow rate of 15 liters/minute using a Next Generation Impactor (Copley Scientific, Inc., United Kingdom). Two samples from each formulation are then analyzed by gravimetric and ultraviolet assays.

For gravimetric assays, the weight of the particles on each impactor plate is determined by calculating the weight difference of each plate before and after nebulization. This assay, which provides a particle distribution based on the liquid droplet weight that accumulates on each plate, is then used in calculations for determining droplet particle size distribution.

For UV assays, material on each impactor plate is collected and antibody concentration determined by UV absorbance. The net distribution of antibody is then calculated. This assay, which provides a particle distribution based on the amount of protein that accumulates on each plate, may be compared to the distribution of particle droplet weight determined by the gravimetric assay.

Histograms of particle size distribution for formulations 1, 2 and 3, respectively, based on an antibody preparation previously prepared against another antigen are expected to remain unchanged for or be minimally impacted by the antibodies used herein. All formulations generate particle sizes (MMAD) less than 5 µm (4.24 µm-4.90 µm), indicating that the formulations are suitable for administration into the respiratory tract, including deep lung penetration. In addition, the geometric standard deviation (GSD) values for an anti-DNABII antibody are expected to range from 1.70 to 2.25, further indicating a particle size distribution suitable to achieve a high local therapeutic protein concentration deep in the respiratory tract of humans.

Moreover, as indicated in Table 2, below, nebulized samples from all formulations demonstrate the ability to bind DNABII protein homologs from *Staphylococcus aureus* (Sa), *Pseudomonas aeruginosa* (Pa), *Klebsiella pneumoniae* (Kp), *Acinetobacter baumannii* (Ab) and *Haemophilus influenzae* (Hi). These five are of particular utility since they span a substantial portion of the diversity in sequences of the DNABII family. Four of these, Sa, Kp, Ab, and Pa are members of the clinically problematic ESKAPE set defined by the US National Institute of Allergy and Infectious Diseases (NIAID), which comprise *Enterobacter aerogenes, Staphylococcus aureus, Klebsiella pneumoniae, Acinetobacter baumannii, Pseudomonas aeruginosa* and *Escherichia coli*. HU-beta of *S. aureus* finds particular use in the assay.

Further, the amount of antibody which exhibits DNABII-binding ability before nebulization is comparable within experimental limits to the amount of antibody that exhibits DNABII binding after nebulization.

TABLE 2

Concentrations of anti-DNABII antibody that bind to DNABII proteins before and after nebulization[2]

| Amount of PS-20 in formulation (20 mM histidine buffer, 115 mM NaCl and PS-20, pH 6.5) | Antibody | Pre-Neb[3] (mg/mL) | Post-Neb[4] (mg/L) |
|---|---|---|---|
| 0.02% | TRL1068 | about 15-20 | comparable |
|  |  | about 15-20 | comparable |
| 0.05% |  | about 15-20 | comparable |
|  |  | about 15-20 | comparable |
| 0.02% | TRL1330 | about 15-20 | comparable |
|  |  | about 15-20 | comparable |
| 0.05% |  | about 15-20 | comparable |
|  |  | about 15-20 | comparable |
| 0.02% | TRL1337 | about 15-20 | comparable |
|  |  | about 15-20 | comparable |
| 0.05% |  | about 15-20 | comparable |
|  |  | about 15-20 | comparable |

[2]Determined by ELISA
[3]Pre-Neb = pre-nebulization
[4]Post-Neb = post-nebulization Example 2

Storage

ELISA

A formulation of the disclosure is also assessed for its ability to stabilize antibody and to allow for activity after storage. To assess these properties, a solution is initially prepared, which contains 20 mM histidine-chloride buffer, 115 mM NaCl and 0.02% (v/v) polysorbate 20, pH 6.5. TRL1068 (18.6 mg/mL), TRL1330 (18.3 mg/mL) and TRL1337 (18.1 mg/mL) singly or as combinations thereof is then added to the solution. The formulation is subsequently stored for three months at 2° C. to 8° C. or −70° C. to determine short term stability. After storage, the formulation is subjected to ELISA and the concentration of each antibody retaining binding ability is determined.

Table 3 describes the expected concentrations of each of the three antibodies, TRL1068, TRL1330, TRL1337, before and after storage. The after storage measured concentrations are comparable to the before storage nominal concentrations within experimental limits. Further, the concentrations after storage, as determined by ELISA, indicates the amount of each antibody that retains antigen-binding ability. Accordingly, the present formulations may be used to stabilize antibodies during storage for at least three months without apparent loss of activity.

TABLE 3

Formulation buffer concentrations of TRL1068, TRL1330 or TRL1337 after three months storage

| Antibody | Storage Temperature | Theoretical concentration prior to storage (mg/mL) | ELISA Concentration (mg/mL) |
|---|---|---|---|
| TRL1068 | 2° C.-8° C. | About 18 | comparable |
|  | −70° C. |  | comparable |
| TRL1330 | 2° C.-8° C. | About 18 | comparable |
|  | −70° C. |  | comparable |
| TRL1337 | 2° C.-8° C. | About 18 | comparable |
|  | −70° C. |  | comparable |

UV

In order to assess the antibody concentration in the formulation after storage more accurately than that determined by ELISA, the concentration of total antibody is determined directly using UV absorbance. As indicated in Table 4, below, the nominal concentration of the total amount of antibody before storage (about 20 mg/mL) is comparable to the concentration of the total antibody determined using UV absorbance after three months at 2° C.-8° C. (about 20 mg/mL) and −70° C. (about 20 mg/mL). Accordingly, these assays are suitable to establish that there is no apparent degradation of the antibodies during the storage conditions when formulated in accordance with the present disclosure.

Table 4 further indicates that, unlike the formulation before storage, granular particles are expected to be visually observed in the formulations after storage. Nevertheless, when ELISA data demonstrate that antibody activity is retained after storage, it is apparent that aggregation is not impacting the bioactivity. Further, as also noted in Table 4, the pH is maintained during storage, thus further supporting that the present formulation is effective in maintaining conditions during storage sufficient to stabilize the antibodies.

TABLE 4

Concentration, Appearance and pH of Antibody combination
(TRL1068, TRL1330 and TRL1337) in the
present formulation after storage

| | | T = 3 months | |
|---|---|---|---|
| Method | T = 0 | 2-8° C. | −70° C. |
| UV | About 20 mg/mL | About 20 mg/mL | About 20 mg/mL |
| Appearance | No particles | Granular particles | Granular particles |
| pH | 6.5 | 6.5 | 6.5 |

Example 3

Safety and Efficacy

Sprague Dawley rats are used to conduct a single dose inhalation safety, toxicity and toxicokinetic (TK) profile study of the antibodies, TRL1068, TRL1330 and TRL1337, alone or in combination in the formulation according to the present disclosure. Initially, the aerosol generation conditions are established. Reproducible aerosol is generated in a side-stream nebulizer using 20 mg/mL of the antibody formulation being tested, resulting in an aerosol concentration of about 1.2 mg/mL and a total dosage of about 150 mg/mL over a six hour exposure period.

The generated atmospheres and particle size distributions are deemed acceptable for the rat inhalation studies. The oxygen concentration and temperature range of the generated atmospheres is about 20-25% and 19-24° C., respectively, with a relative humidity between 42.0% and 71.0%. Further, the particle size distribution indicates that the aerosols are respirable (MMAD about 2 μm, GSD about 2 μm).

Groups of Sprague Dawley rats are exposed to a single nose-only inhalation of a liquid aerosol comprising the antibody or antibody combination formulation or vehicle control. As shown below in Table 5, rats are exposed to the aerosolized formulations for 90 minutes (low dose), 180 minutes (mid dose) and 360 minutes (high dose and vehicle control).

TABLE 5

Single Inhalation Administration to Sprague Dawley rats

| Grp No. | Group Designation | Exposure Duration (mins) | Target Total Delivered Dose Level (mg/kg) | Target Aerosol Concentration of antibody combination (mg/L)[a] | Toxicology Main Animals Males | TK Animals Males |
|---|---|---|---|---|---|---|
| 1 | Vehicle Control | 360 | 0 | 0 | 6 | 6 |
| 2 | Low Dose | 90 | About 81 | About 1.2 | 6 | 9 |
| 3 | Mid Dose | 180 | About 160-175 | About 1.2 | 6 | 9 |
| 4 | High Dose | 360 | About 300-350 | About 1.2 | 6 | 9 |

[a]Targeted aerosol concentrations are calculated based on an estimated body weight of 0.250 kg.

The mean achieved test atmosphere concentrations of the antibody formulation, as assessed by chemical determination, are as follows.

TABLE 6

Test Atmosphere Concentration and Estimated Achieved Dose Levels

| Group No. | Group Designation | Mean Test Atmosphere Concentration (mg/L) | | SD | % RSD | % of Target Achieved |
|---|---|---|---|---|---|---|
| | | Targeted | Achieved | | | |
| 1 | Vehicle Control | 0.0 | BLQ | NA | NA | NA |
| 2 | Low Dose | 1.2 | About 0.94-0.99 | About 0.11-0.12 | About 11-12 | About 75-85 |

TABLE 6-continued

| | | Test Atmosphere Concentration and Estimated Achieved Dose Levels | | | | |
|---|---|---|---|---|---|---|
| Group No. | Group Designation | Mean Test Atmosphere Concentration (mg/L) Targeted | Achieved | SD | % RSD | % of Target Achieved |
| 3 | Mid Dose | 1.2 | About 0.94-0.99 | About 0.11-0.12 | About 11-12 | About 75-85 |
| 4 | High Dose | 1.2 | About 0.94-0.99 | About 0.11-0.12 | About 11-12 | About 75-85 |

SD = Standard Deviation,
RSD = Relative Standard Deviation
BLQ: Below limit of quantification,
NA: Not applicable
% of Target Achieved = (Mean Achieved aerosol concentration/Targeted aerosol concentration) × 100

Particle size distributions of the aerosolized vehicle control, as assessed by gravimetric determination, for Group 1 and by chemical determination for Groups 2 to 4 are as follows.

12.9 mg/kg (Group 3) and 255 mg/kg, 25.5 mg/kg (Group 4). The overall estimated achieved total and pulmonary doses are about 75%, 80% and 79% of the targeted dose levels for the low, mid and high dose groups, respectively.

TABLE 8

| | | | Estimated Overall Achieved Doses on Day 1 | | | |
|---|---|---|---|---|---|---|
| Group No. | Target Pulmonary Dose Level (mg/kg) | Target Total Delivered Dose Level (mg/kg) | Mean Body Weight* (kg) | Estimated Achieved Pulmonary Dose Level** (mg/kg) | Estimated Achieved Total Delivered Dose Level (mg/kg) | % Accuracy |
| 1 | 0 | 0 | About 0.30 | 0 | 0 | NA |
| 2 | 8 | 80 | About 0.30 | About 6.0 | About 60 | About 75 |
| 3 | 16 | 160 | About 0.30 | About 12.0 | About 120 | About 80 |
| 4 | 32 | 320 | About 0.30 | About 25.0 | About 250 | About 78 |

*Mean body weight collected from Day 1 is used for estimation.
**Estimated achieved lung dose levels are calculated as 10% of the respective estimated achieved inhaled dose level of the TRL1068, TRL1330 and TRL1337 combination.

TABLE 7

| | Particle Size Distribution (PSD) Measurements. | |
|---|---|---|
| | Particle Size | |
| Group No. | MMAD (μm) | GSD |
| 1 | 4.0 | 2.1 |
| 1 | 2.8 | 1.8 |
| 1 | 2.0 | 2.1 |
| 2 | 1.9 | 1.9 |
| 2 | 1.4 | 2.4 |
| 3 | 2.0 | 1.8 |
| 4 | 1.8 | 1.9 |

MMAD = Mass median aerodynamic diameter.
GSD = Geometric standard deviation.

The particle size distribution measurements confirm that the antibody or antibody combination in the aerosolized test item is respirable for the rat. The deposition within the respiratory tract is considered to be 100% as the mean Mass Median Aerodynamic Diameters (MMAD) are ≤2.0 μm with corresponding geometric standard deviations (σg) <2.5 for Groups 2, 3 and 4. Similarly, the aerosolized vehicle control for Group 1 is considered respirable with the MMAD ranging between 2.0 to 4.0 μm and GSD ranging between 1.8 and 2.1.

As shown in Table 8, below, the following delivered total and pulmonary dosages, respectively, are estimated for each of the groups: 62 mg/kg, 6.2 mg/kg (Group 2), 129 mg/kg, The highest concentration of TRL1068, TRL1330 and TRL1337 in the lungs is detected at 4 hours post dose. The concentrations of TRL1068, TRL1330 or TRL1337 in the lungs declines gradually, but are still significantly higher than Below the Limit of Quantification (BLQ: 10.3 ng/mL) at the last collection time (168 hours post dose). Further, TRL1068, TRL1330 and TRL1337 levels in the right caudal lobe are similar to those of the right cranial lobe, confirming that the antibody formulation can be delivered throughout the lung. The concentration of TRL1068, TRL1330 and TRL1337 increase with increasing dosage level and at a given dose level, the concentrations of TRL1068, TRL1330 and TRL1337 are comparable.

Systemic exposure to the TRL1068, TRL1330 and TRL1337 antibodies and combinations thereof increase in a less than dose proportional manner for all groups. However, the Cmax between the mid and high doses of TRL1330 increases proportionally to the dose (about 2-fold). At all dose levels, the exposure to TRL1068, TRL1330 and TRL1337 is similar, ranging from 1.0 to 1.5-fold between each antibody.

There are no related clinical signs or clear effects on body weight or food consumption, ophthalmoscopy, respiratory parameter measurements or clinical pathology (hematology, coagulation, clinical chemistry and urinalysis) in any treated group.

In conclusion, based on the parameters examined, the formulation and the antibodies have no adverse effect observed at the highest tested dose (255 mg/kg). Consequently, the No Observed Adverse Effect Level (NOAEL) is considered to be at the achieved total delivered dose level for male rats when dosed for a single exposure by nose-only inhalation for 360 minutes.

Example 4

Antibody Against DNABII Protein Binds to Biofilm

Localization of fluorescently tagged TRL1068 was examined using VivoTag® 680XL and fluorescent confocal microscopy. Biofilm of Xen36 *S. aureus* was grown on 0.1 mm diameter stainless steel spinal implants for 24 hours. Experimental groups were: (A) biofilm covered implant alone (infected control); (B) biofilm covered implant exposed to fluorescent probe alone (no antibody); (C) biofilm covered implant exposed to fluorescently tagged IgG isotype control antibody; and (D) biofilm covered implant exposed to fluorescently tagged TRL1068. All implants were exposed to their respective fluorescently tagged antibody or control for 15 minutes, washed with PBS, and then imaged using fluorescent confocal microscopy. Images (FIG. 2) show minimal background fluorescence for groups A-C and fluorescence along the length of the pin for group D, confirming binding of TRL1068 to biofilm.

Example 5

Nebulizer Delivery of TRL1068 to the Lungs

*Pseudomonas aeruginosa* (PA) is the leading cause of morbidity and mortality in patients with ventilator-associated pneumonia (VAP) and cystic fibrosis (CF) [2-6]. While these conditions involve different pathological processes, both are strongly associated with biofilm and both are highly resistant to antibiotic treatment. In a very informative study of PA biofilm dynamics, Haagensen et al. [3] have shown that newly formed (1 day) PA biofilms are over 10-fold more resistant to antibiotic treatment, but are still responsive to antibiotic treatment; older (3 day) biofilms, on the other hand, require much longer times of treatment by high dose antibiotic to see a therapeutic effect. Clinical investigators of CF routinely report that established infections of CF are impossible to treat. Both VAP and infection during CF show strong indications of initiation in the upper respiratory tract, with biofilm associated bacteria later migrating into the lungs to cause pneumonia in VAP and acute exacerbations in CF. Both of these conditions are complex, especially CF, involving bacterial evolution and accumulation of pathological alterations during chronic infection. Thus, the design of preclinical models to validate promising therapeutics is challenging [2]. However, a model providing a mature PA biofilm in the upper airways of the mouse, Mouse Respiratory Chronic Infection Model (MRCIM), with continual PA seeding into the lower airways, has been established by Prof. Aras Kadioglu at the University of Liverpool [1,7]. The model delivers inhaled clinical strains of PA into the airways, allowing long term chronic infection of both the upper and lower airways for up to 35 days (and beyond), post-infection.

FIG. 1 shows PA infection in both the lungs and the nasopharynx (upper respiratory). The persistence of PA in the nasopharynx is interpreted, based on gene expression patterns, as being associated with a biofilm-associated colony structure.

TRL1068 has been shown to disrupt the biofilm of PA in vitro, with concentrations of antibody easily achieved in animals [Estellés A, Woischnig A K, Liu K, Stephenson R, Lomongsod E, Nguyen D, Zhang J, Heidecker M, Yang Y, Simon R J, Tenorio E, Ellsworth S, Leighton A, Ryser S, Gremmelmaier N K, Kauvar L M. A High-Affinity Native Human Antibody Disrupts Biofilm from *Staphylococcus aureus* Bacteria and Potentiates Antibiotic Efficacy in a Mouse Implant Infection Model. *Antimicrob Agents Chemother.* 60 (4):2292-301 (2016)]. In addition, all of the models used to test TRL1068 in vivo thus far have shown treatment improvement, including for Gram negative species.

Figures 2A, 2C:
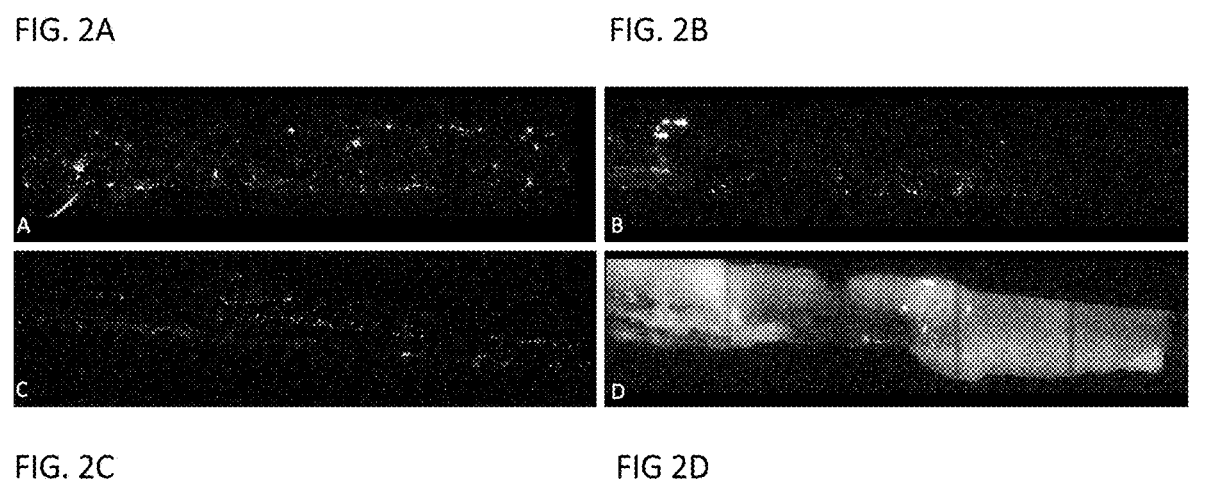

FIG. 2 shows that TRL1068 binds to biofilm on a surface.

Example 6

Respiratory Infection of the Mouse by PA and Treatment with TRL1068

The MRCIM model uses a biofilm forming, lung adapted PA Liverpool Epidemic Strain (NP612) from a CF patient. As the bacteria adapt to the in vivo environment, infectivity of the lungs increases. Thus, at day 3, lung CFUs are low but then increase over the next several days as the biofilm reservoir becomes established, resulting in shedding of bacteria into the airways.

Figure 3A:
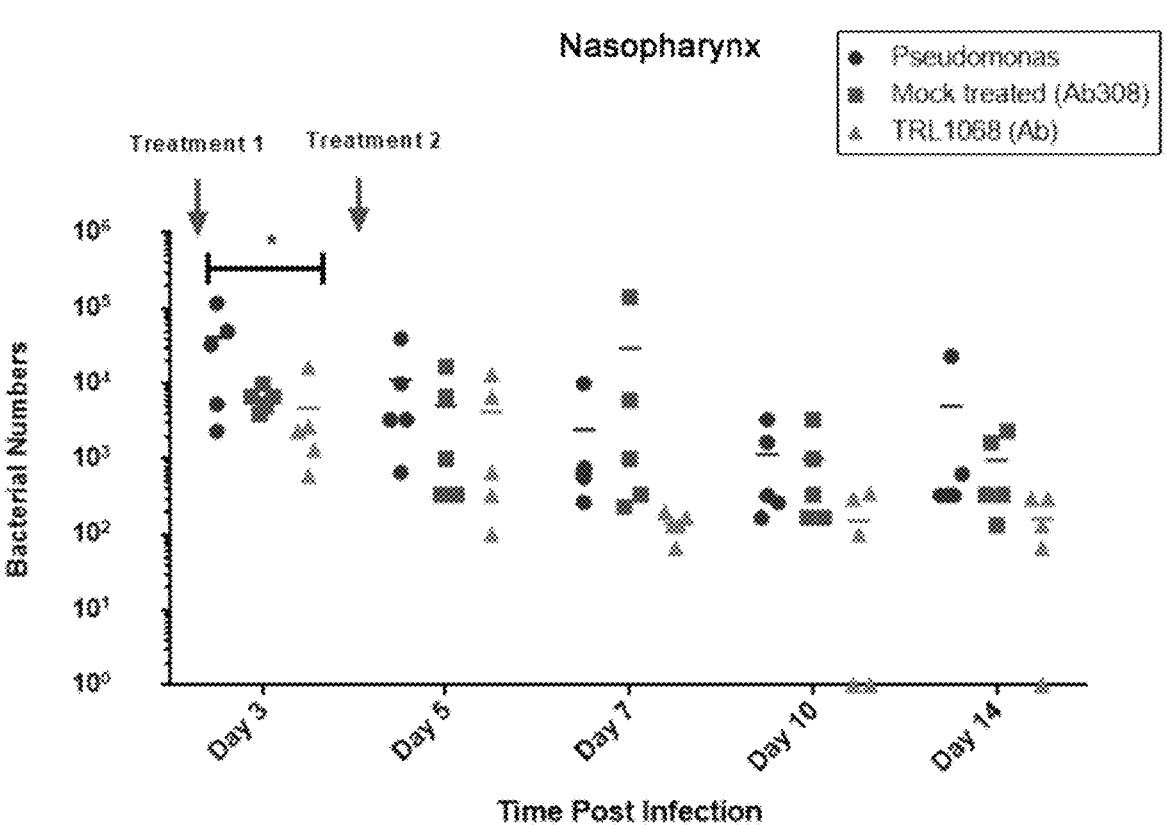
FIGS. 3A and 3B are graphs depicting comparative bacterial number reduction in the nasopharynx (FIG. 3A) and lung (FIG. 3B) in MRCIM in response to intranasal administration of TRL1068, Ab308 (mock treatment with an isotype matched mAb that does not bind to biofilm components), and untreated (*Pseudomonas*). Mice were inoculated at day 1 with a clinical strain of *P. aeruginosa* known to form biofilm. Antibody treatment was on day 2 and day 4.
Figure 3B:
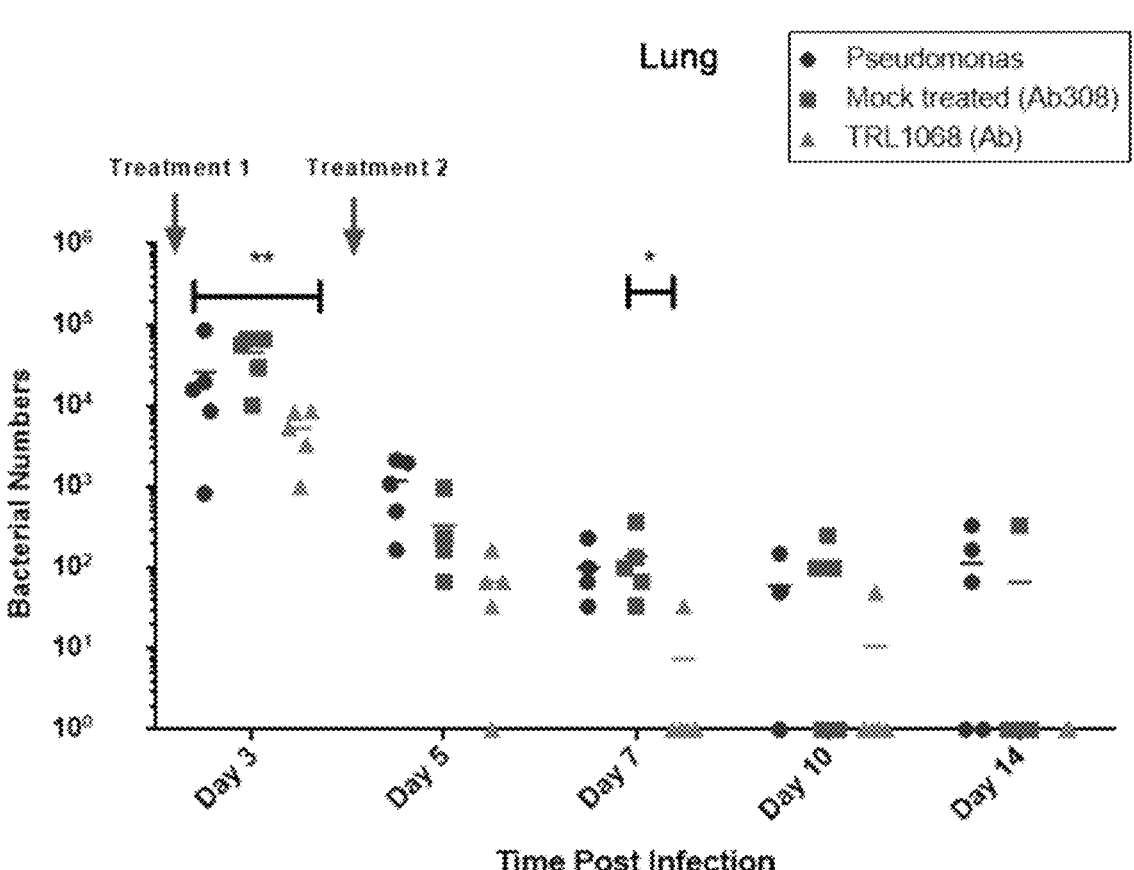
Figure 4A:
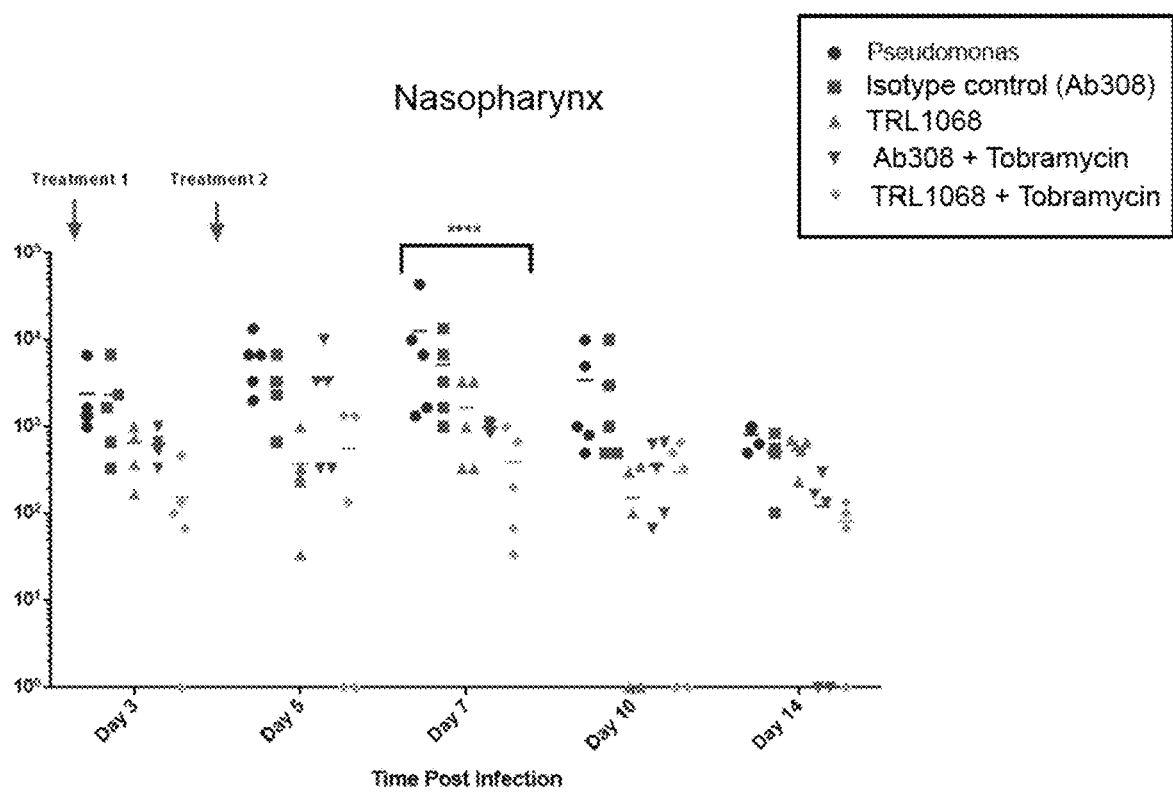
FIGS. 4A-4D show bacterial CFUs in nasopharynx (FIGS. 4A and 4C) and lung (FIGS. 4B and 4D) of mice inoculated then treated intranasally on days 2 and day 4 with isotype control mAb Ab308 (1 mg/kg), TRL1068 (1 mg/kg), Ab308 plus tobramycin (1 mg/kg each) or TRL1068 plus tobramycin (1 mg/kg each), and untreated (*Pseudomonas*).
Figure 4B:
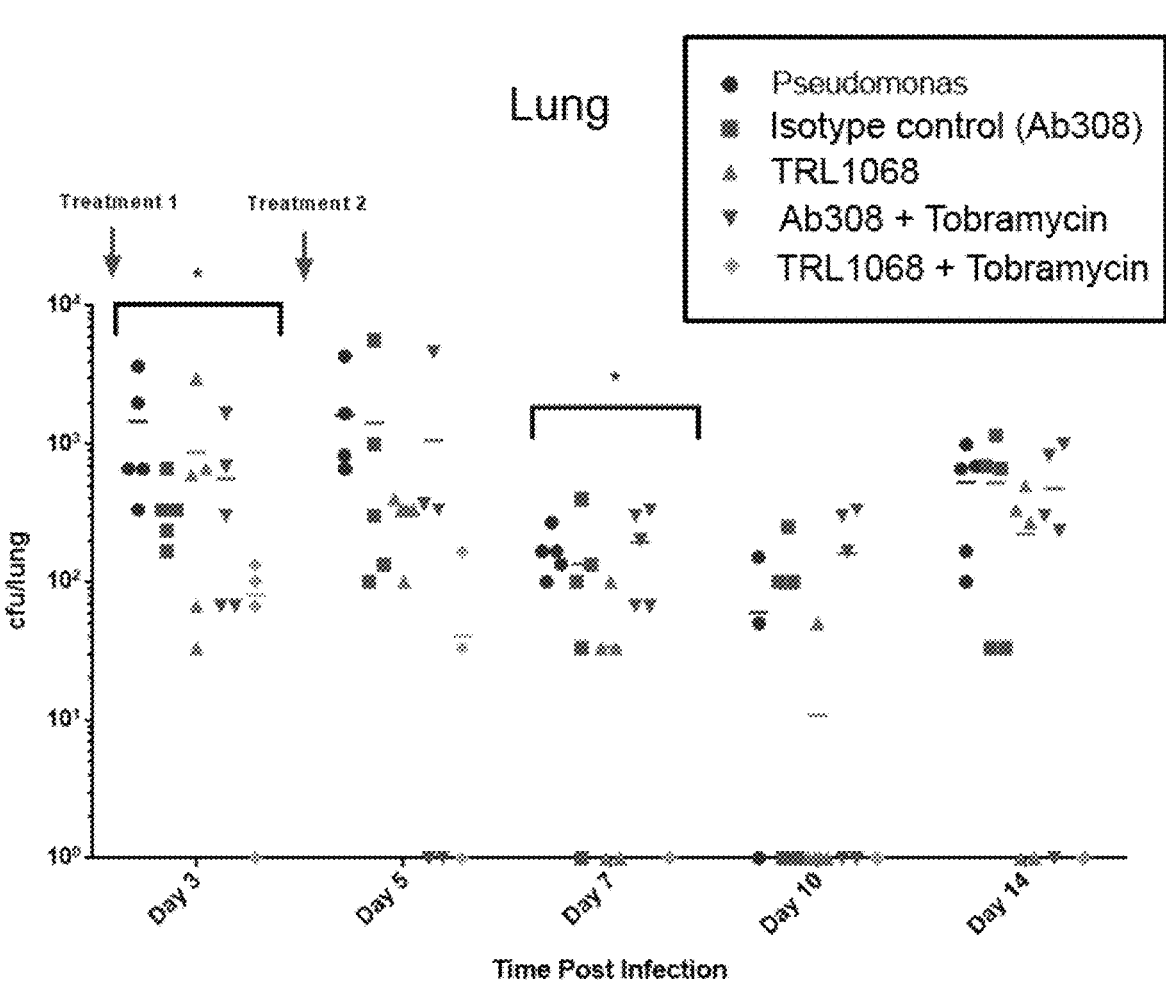
Figure 4C:
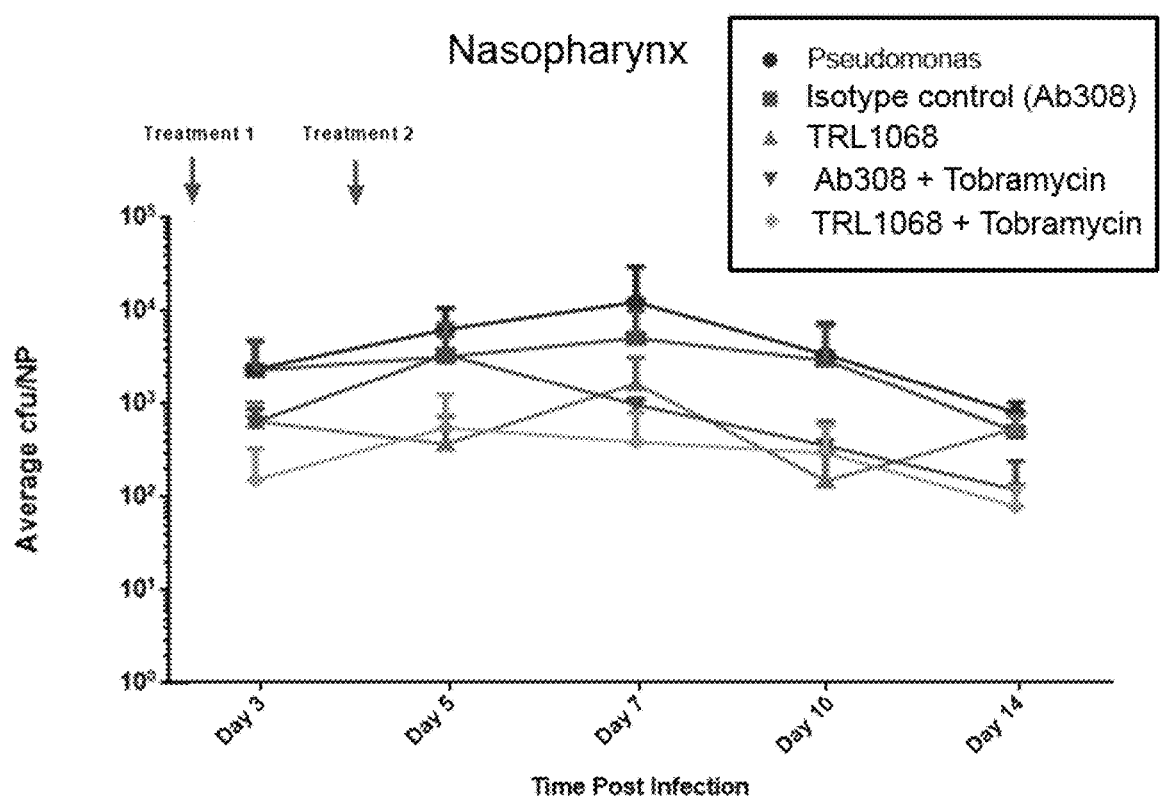
Figure 4D:
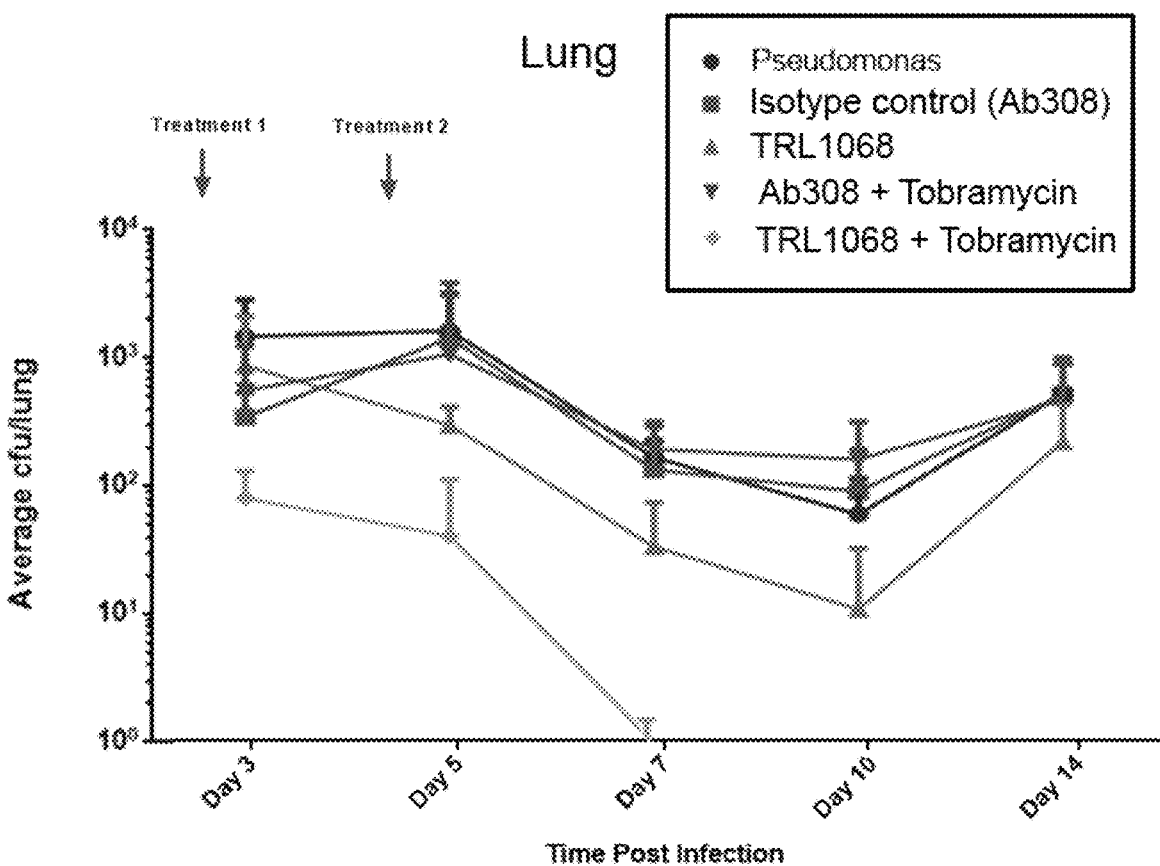

Male and Female BALB/cOlaHsd mice between 9 and 12 weeks of age are infected by intra-nasal instillation with a fresh mid-log phase dose of $2 \times 10^6$ CFU. TRL1068 is administered intranasally (50 µL) at 1 mg/kg on days 2 and 4, and bacterial CFUs are measured in the nasopharynx and in the lung. Efficacy is indicated by reductions of CFUs by 1-2 logs. Further enhancement of efficacy is assessed following co-administration of bactericidal antibiotics. To control for non-specific effects of high doses of IgG, an isotype control mAb is used. In addition to CFUs, body weight is recorded. After sacrifice to measure CFUs, cytokines are measured, and samples are examined by histological analysis. As shown in FIG. 3, TRL1068 alone reduced the bacterial burden in the nasopharynx, accompanied by reduction in bacterial burden in the lungs.

Example 7

Respiratory Infection of the Mouse by PA and Treatment With TRL1068 and Antibiotic as Adjunctive Therapy As shown in FIG. 4, including an antibiotic (tobramycin) along with TRL1068 substantially improved the reduction in bacterial load. In this 14 day experiment, CFUs for the indicated treatment groups are shown in nasopharynx (a) and lungs (b). The general trend of average cfu/tissue is shown in c) nasopharynx and d) lungs. Mice (n=5 per group) were infected intranasally with $2 \times 10^6$ cfu/ml of strain NP162. Mice were treated intranasally with either TRL1068 or isotype control Ab308 on day 2 and day 4; *p<0.05 **p<0.01. At day 7, a rebound in CFU in the nasopharynx is seen for TRL1068 alone, as bacteria released from the biofilm begin to grow planktonically. In the lungs, the combination of TRL1068 with tobramycin was highly effective at eradicating the infection. Thus, TRL1068 and tobramycin exhibited a synergistic activity in reducing *Pseudomonas* load.

It is understood that tobramycin inhaled solution (TIS) was approved by the FDA in 1998 for *Pseudomonas* infections. In 2010, the FDA approved Aztreonam Lysine inhaled solution (AZLI). Administering these inhaled drugs along with inhaled TRL1068 is within the scope of the invention.

It is also understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

---

SEQUENCE LISTING FREE TEXT

---

(the variable region of the TRL1068 heavy chain
(SEQ ID NO: 1) from U.S. Pat. No. 10,233,234)

SEQ ID NO: 1

```
Gln Val Gln Leu Val Glu Ser Gly Pro Gly Leu Val Lys Pro Ser Glu
1               5               10              15

Thr Leu Ser Leu Thr Cys Arg Val Ser Gly Asp Ser Asn Arg Pro Ser
        20              25              30

Tyr Trp Ser Trp Ile Arg Gln Ala Pro Gly Lys Ala Met Glu Trp Ile
        35              40              45

Gly Tyr Val Tyr Asp Ser Gly Val Thr Ile Tyr Asn Pro Ser Leu Lys
    50              55              60

Gly Arg Val Thr Ile Ser Leu Asp Thr Ser Lys Thr Arg Phe Ser Leu
65              70              75              80

Lys Leu Thr Ser Val Ile Ala Ala Asp Thr Ala Val Tyr Tyr Cys Ala
            85              90              95

Arg Glu Arg Phe Asp Arg Thr Ser Tyr Lys Ser Trp Trp Gly Gln Gly
            100             105             110

Thr Gln Val Thr Val Ser Ser
        115
```

(the variable region of the heavy chain of TRL1330
(SEQ ID NO: 21) from U.S. Pat. No. 10,233,234)

SEQ ID NO: 2

```
Gln Val Gln Leu Val Glu Ser Gly Thr Glu Val Lys Asn Pro Gly Ala
1               5               10              15

Ser Val Lys Val Ser Cys Thr Ala Ser Gly Tyr Lys Phe Asp Glu Tyr
            20              25              30

Gly Val Ser Trp Val Arg Gln Ser Pro Gly Gln Gly Leu Glu Trp Met
        35              40              45

Gly Trp Ile Ser Val Tyr Asn Gly Lys Thr Asn Tyr Ser Gln Asn Phe
    50              55              60

Gln Gly Arg Leu Thr Leu Thr Thr Glu Thr Ser Thr Asp Thr Ala Tyr
65              70              75              80

Met Glu Leu Thr Ser Leu Arg Pro Asp Asp Thr Ala Val Tyr Tyr Cys
            85              90              95

Ala Thr Asp Lys Asn Trp Phe Asp Pro Trp Gly Pro Gly Thr Leu Val
            100             105             110

Thr Val Ser Ser
        115
```

(the variable region of the heavy chain of TRL1337
(SEQ ID NO: 25) from U.S. Pat. No. 10,233,234)

SEQ ID NO: 3

```
Gln Val Gln Leu Leu Glu Ser Gly Pro Gly Leu Val Lys Pro Ser Glu
1               5               10              15

Thr Pro Ser Leu Thr Cys Thr Val Ser Gly Gly Ser Ile Arg Ser Tyr
            20              25              30

Tyr Trp Ser Trp Ile Arg Gln Pro Pro Gly Lys Gly Leu Glu Trp Ile
        35              40              45

Gly Tyr Ile Tyr Tyr Ser Gly Ser Thr Asn Tyr Asn Pro Ser Leu Lys
    50              55              60

Ser Arg Val Thr Ile Ser Val Asp Met Ser Lys Asn Gln Phe Ser Leu
65              70              75              80
```

-continued

---

SEQUENCE LISTING FREE TEXT

---

```
Lys Leu Ser Ser Val Thr Ala Ala Asp Thr Ala Met Tyr Tyr Cys Ala
                85                  90                  95

Arg Val Tyr Gly Gly Ser Gly Ser Tyr Asp Phe Asp Tyr Trp Gly Gln
            100                 105                 110

Gly Thr Leu Val Thr Val Ser Ser
        115                 120

(the variable region of the light chain of TRL1068
(SEQ ID NO: 2) from U.S. Pat. No. 10,233,234)
                                                      SEQ ID NO: 4
Asp Ile Val Leu Thr Gln Ala Pro Gly Thr Leu Ser Leu Ser Pro Gly
 1               5                  10                  15

Asp Arg Ala Thr Leu Ser Cys Arg Ala Ser Gln Arg Leu Gly Gly Thr
            20                  25                  30

Ser Leu Ala Trp Tyr Gln His Arg Ser Gly Gln Ala Pro Arg Leu Ile
        35                  40                  45

Leu Tyr Gly Thr Ser Asn Arg Ala Thr Asp Thr Pro Asp Arg Phe Ser
    50                  55                  60

Gly Ser Gly Ser Gly Thr Asp Phe Val Leu Thr Ile Ser Ser Leu Glu
65                  70                  75                  80

Pro Glu Asp Phe Ala Val Tyr Tyr Cys Gln Gln Tyr Gly Ser Pro Pro
            85                  90                  95

Tyr Thr Phe Gly Gln Gly Thr Thr Leu Asp Ile Lys
            100                 105

(the variable region of the light chain of TRL1330
(SEQ ID NO: 22) from U.S. Pat. No. 10,233,234)
                                                      SEQ ID NO: 5
Asp Ile Val Leu Thr Gln Ser Pro Ser Ala Ser Gly Ser Pro Gly Gln
 1               5                  10                  15

Ser Ile Thr Ile Ser Cys Thr Gly Thr Asn Thr Asp Tyr Asn Tyr Val
            20                  25                  30

Ser Trp Tyr Gln His His Pro Gly Lys Ala Pro Lys Val Ile Ile Tyr
        35                  40                  45

Asp Val Lys Lys Arg Pro Ser Gly Val Pro Ser Arg Phe Ser Gly Ser
    50                  55                  60

Arg Ser Gly Asn Thr Ala Thr Leu Thr Val Ser Gly Leu Gln Thr Glu
65                  70                  75                  80

Asp Glu Ala Asp Tyr Tyr Cys Val Ser Tyr Ala Asp Asn Asn His Tyr
            85                  90                  95

Val Phe Gly Ser Gly Thr Lys Val Thr Val Leu
            100                 105

(the variable region of the light chain of TRL1337
(SEQ ID NO: 26) from U.S. Pat. No. 10,233,234)
                                                      SEQ ID NO: 6
Asp Ile Val Leu Thr Gln Ser Pro Ser Ala Ser Gly Ser Pro Gly Gln
 1               5                  10                  15

Ser Val Thr Ile Ser Cys Thr Gly Thr Ser Ser Asp Val Gly Gly Tyr
            20                  25                  30

Asn Tyr Val Ser Trp Tyr Gln Gln Leu Pro Gly Lys Ala Pro Lys Leu
        35                  40                  45

Met Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Phe Ala Gly Ser
```

-continued

| SEQUENCE LISTING FREE TEXT |
| --- |

|     |     |     | 85  |     |     |     |     | 90  |     |     |     |     | 95  |     |
| --- | --- | --- | --- | --- | --- | --- | --- | --- | --- | --- | --- | --- | --- | --- |
| Asn | Asn | His | Val | Val | Phe | Gly | Gly | Gly | Thr | Lys | Leu | Thr | Val | Leu |
|     |     |     | 100 |     |     |     |     | 105 |     |     |     |     | 110 |     |

CITATION LIST

Non-Patent Literature

[1] Fothergill, J. L., D. R. Neill, N. Loman, C. Winstanley, and A. Kadioglu, *Pseudomonas aeruginosa* adaptation in the nasopharyngeal reservoir leads to migration and persistence in the lungs. Nat Commun, 2014. 5: p. 4780.

[2] Bielen, K., B. s Jongers, S. Malhotra-Kumar, P. G. Jorens, H. Goossens, and S. Kumar-Singh, *Animal models of hospital-acquired pneumonia: current practices and future perspectives*. Ann Transl Med, 2017. 5 (6): p. 132.

[3] Haagensen, J., D. Verotta, L. Huang, J. Engel, A. M. Spormann, and K. Yang, *Spatiotemporal pharmacodynamics of meropenem- and tobramycin-treated Pseudomonas aeruginosa biofilms*. J Antimicrob Chemother, 2017. 72 (12): p. 3357-3365.

[4] Hamilos, D. L., Biofilm Formations in Pediatric Respiratory Tract Infection Part 2: Mucosal Biofilm Formation by Respiratory Pathogens and Current and Future Therapeutic Strategies to Inhibit Biofilm Formation or Eradicate Established Biofilm. Curr Infect Dis Rep, 2019. 21 (2): p. 8.

[5] Loo, C. Y., W. H. Lee, P. M. Young, R. Cavaliere, C. B. Whitchurch, and R. Rohanizadeh, *Implications and emerging control strategies for ventilator-associated infections*. Expert Rev Anti Infect Ther, 2015. 13 (3): p. 379-93.

[6] Wenzler, E., D. R. Fraidenburg, T. Scardina, and L. H. Danziger, *Inhaled Antibiotics for Gram-Negative Respiratory Infections*. Clin Microbiol Rev, 2016. 29 (3): p. 581-632.

[7] Bricio-Moreno, L., V. H. Sheridan, I. Goodhead, S. Armstrong, J. K. L. Wong, E. M. Waters, J. Sarsby, S. Panagiotou, J. Dunn, A. Chakraborty, Y. Fang, K. E. Griswold, C. Winstanley, J. L. Fothergill, A. Kadioglu, and D. R. Neill, *Evolutionary trade-offs associated with loss of PmrB function in host-adapted Pseudomonas aeruginosa*. Nat Commun, 2018. 9 (1): p. 2635.

[8] Waters, E. M., D. R. Neill, B. Kaman, J. S. Sahota, M. R. J. Clokie, C. Winstanley, and A. Kadioglu, *Phage therapy is highly effective against chronic lung infections with Pseudomonas aeruginosa*. Thorax, 2017. 72 (7): p. 666-667.

[9] Carter, M. E., J. L. Fothergill, M. J. Walshaw, K. Rajakumar, A. Kadioglu, and C. Winstanley, A subtype of a *Pseudomonas aeruginosa* cystic fibrosis epidemic strain exhibits enhanced virulence in a murine model of acute respiratory infection. J Infect Dis, 2010. 202 (6): p. 935-42.

[10] Dell, R. B., S. Holleran, and R. Ramakrishnan, *Sample size determination*. Ilar j, 2002. 43 (4): p. 207-13.

[11] Altschul, et al. (1990) J. Mol. Bio. 215:403-410

[12] Ausubel, F M et al. (1993) *Current Protocols in Molecular Biology* John Wiley & Sons, New York, N.Y., 1993.

[13] Sambrook et al., MOLECULAR CLONING: A LABORATORY MANUAL (Second Edition), Cold Spring Harbor Press, Plainview, N.Y., 1989

Patent Literature

[14] U.S. Pat. No. 10,233,234—BINDING MOIETIES FOR BIOFILM REMEDIATION—Kauvar et al., granted 19 Mar. 2019.

[15] WO 2009/027095—AEROSOLS FOR SINUNASAL DRUG DELIVERY—Keller et al., published 5 Mar. 2009.

[16] WO 2011/134940—OPERATING METHOD FOR AN AEROSOL DELIVERY DEVICE AND AEROSOL DELIVERY DEVICE—Krüner et al., published 3 Nov. 2011.

[17] WO 2014/152841—COMPOSITION AND METHODS BASED ON NEUTRALIZING ANTIBODIES DELIVERED INTRANASALLY FOR ENHANCED THERAPEUTIC EFFICACY—Wittekind and Vigil, published 25 Sep. 2014, issued as U.S. Pat. No. 9,718,875 (1 Aug. 2017).

[18] WO 2015/048484—BINDING MOIETIES FOR BIOFILM REMEDIATION—Kauvar et al., published 2 Apr. 2015.

[19] WO 2015/120097—ANTIBODIES USEFUL IN PASSIVE INFLUENZA IMMUNIZATION, AND COMPOSITIONS, COMBINATIONS AND METHODS FOR USE THEREOF—Estelies et al., published 13 Aug. 2015.

What is claimed is:

1. A stable aqueous therapeutic protein formulation comprising:
(i) one or more therapeutic proteins, wherein the one or more therapeutic proteins comprise one or more anti-DNABII antibodies in an amount ranging from 10 to 150 mg/mL, wherein at least one anti-DNABII antibody is selected from the group consisting of
(a) the heavy and the light chain of a first antibody comprises: the TRL 1068 heavy chain CDR sequences HCDR1/HCDR2/HCDR3 (SEQ ID NO: 1) and the TRL 1068 light chain CDR sequences LCDR1/LCDR2/LCDR3 (SEQ ID NO: 4), and/or
(b) wherein the one or more anti-DNABII antibodies binds to the same epitope as the antibody of (a) and comprises a heavy and a light chain, wherein the heavy chain comprises: a polypeptide having at least 90% sequence identity with the TRL1068 heavy chain CDR sequences HCDR1/HCDR2/HCDR3 (SEQ ID NO: 1) and the light chain comprises a polypeptide having at least 90% identity with the TRL1068 light chain CDR sequences LCDR1/LCDR2/LCDR3 (SEQ ID NO: 4); and/or
(c) the heavy and the light chain of a second antibody comprises: the TRL1330 heavy chain CDR sequences HCDR1/HCDR2/HCDR3 (SEQ ID NO: 2) and the TRL1330 light chain CDR sequences LCDR1/LCDR2/LCDR3 (SEQ ID NO: 5);
(d) wherein the one or more anti-DNABII antibodies binds to the same epitope as the antibody of (c) and comprises a heavy and a light chain, wherein the heavy chain comprises: a polypeptide having at least 90% sequence identity with the TRL1330 heavy chain CDR sequences HCDR1/HCDR2/HCDR3 (SEQ ID NO: 2) and the light chain comprises a polypeptide having at least 90% identity with TRL1330 light chain CDR sequences LCDR1/LCDR2/LCDR3 (SEQ ID NO: 5)
(e) the heavy and the light chain of a third antibody comprise: the TRL1337 heavy chain CDR sequences, HCDR1/HCDR2/HCDR3 (SEQ ID NO: 3) and the TRL 1337 light chain CDR sequences (LCDR1/LCDR2/LCDR3 of SEQ ID NO: 6), and
(f) wherein the one or more anti-DNABII antibodies binds to the same epitope as the antibody of (e) and comprises a heavy and a light chain, wherein the heavy chain comprises: a polypeptide having at least 90% sequence identity with the TRL 1337 heavy chain CDR sequences, HCDR1/HCDR2/HCDR3 (SEQ ID NO: 3) and the light chain comprises a polypeptide having at least 90% identity with LCDR1/LCDR2/LCDR3 (SEQ ID NO: 6);
(ii) histidine buffer,
(iii) NaCl,
(iv) an aqueous carrier, and (v) a surfactant,
wherein a pH of the aqueous therapeutic formulation ranges from 5.5-8.0, and wherein the formulation is formulated for respiratory tract delivery and produces particles comprising the one or more therapeutic proteins upon aerosolization.

2. The aqueous therapeutic protein formulation of claim 1, wherein the histidine buffer comprises histidine chloride.

3. The aqueous therapeutic protein formulation of claim 1, wherein the concentration of the therapeutic protein ranges from 30 mg/mL to about 70 mg/mL.

4. The aqueous therapeutic protein formulation of claim 1, wherein the concentration of therapeutic protein is about 20 mg/mL.

5. The aqueous therapeutic protein formulation of claim 1, wherein the NaCl is at a concentration of about 115 mM.

6. The aqueous therapeutic protein formulation of claim 1, wherein the formulation further comprises a non-ionic surfactant.

7. The aqueous therapeutic protein formulation of claim 6, wherein the non-ionic surfactant comprises a polysorbate.

8. The aqueous therapeutic protein formulation of claim 7, wherein the polysorbate comprises polysorbate 20 in an amount of about 0.02%.

9. The aqueous therapeutic protein formulation of claim 1, wherein the pH of the aqueous formulation ranges from 6.0-6.5.

10. The aqueous therapeutic protein formulation of claim 1, wherein the pH of the formulation is about 6.0.

11. The aqueous therapeutic protein formulation of claim 1, wherein histidine is present in the formulation at a concentration of about 20 mM.

12. The aqueous therapeutic protein formulation of claim 1, wherein the one or more anti-DNABII antibodies comprises: a heavy and a light chain comprising, respectively (a1) the TRL1068 heavy chain CDR sequences HCDR1/HCDR2/HCDR3 (SEQ ID NO: 1) and the TRL1068 light chain CDR sequences LCDR1/LCDR2/LCDR3 (SEQ ID NO: 4);

(b1) the TRL 1330 heavy chain CDR sequences HCDR1/HCDR2/HCDR3 (SEQ ID NO: 2) and the TRL1330 light chain CDR sequences LCDR1/LCDR2/LCDR3 (SEQ ID NO: 5); and (c1) the TRL 1337 heavy and the light chain CDR sequences, HCDR1/HCDR2/HCDR3 (SEQ ID NO: 3), and LCDR1/LCDR2/LCDR3 (SEQ ID NO: 6).

13. The aqueous therapeutic protein formulation of claim 1, wherein the one or more anti-DNABII antibodies comprises at least three anti-DNABII antibodies each of which comprises a heavy and light chain, wherein (i) the heavy and the light chain of the first antibody comprises: the TRL1068 heavy chain CDR sequences HCDR1/HCDR2/HCDR3 (SEQ ID NO: 1) and the TRL1068 light chain CDR sequences LCDR1/LCDR2/LCDR3 (SEQ ID NO: 4);

(ii) the heavy and the light chain of the second antibody comprises: the TRL1330 heavy chain CDR sequences HCDR1/HCDR2/HCDR3 (SEQ ID NO: 2) and the TRL1330 light chain CDR sequences LCDR1/LCDR2/LCDR3 (SEQ ID NO: 5); and (iii) the heavy and the light chain of the third antibody comprise: the TRL1337 heavy chain CDR sequences, HCDR1/HCDR2/HCDR3 (SEQ ID NO: 3) and the TRL1337 light chain CDR sequences (LCDR1/LCDR2/LCDR3 of SEQ ID NO: 6).

14. The aqueous therapeutic protein formulation of claim 1, wherein the one or more therapeutic proteins do not lose more than 15% of its biological activity during storage relative to an activity of the therapeutic protein at beginning of storage, wherein storage is at least for 3 month at 2° C.-8° C.

15. The aqueous therapeutic protein formulation of claim 1, wherein the storage is for a period in the range of three month to two years.

16. The aqueous therapeutic formulation according to claim 1, wherein the aqueous therapeutic formulation is a pharmaceutical aqueous therapeutic formulation.

17. The aqueous therapeutic protein formulation of claim 1, further comprising an antibiotic.

18. The aqueous therapeutic protein formulation of claim 17, wherein the antibiotic is an aminoglycoside or monobactam.

19. The aqueous therapeutic protein formulation of claim 18, wherein the aminoglycoside is tobramycin.

20. The aqueous therapeutic protein formulation of claim 18, wherein the monobactam is aztreonam.

\* \* \* \* \*

SEQUENCE LISTING

```
<160> NUMBER OF SEQ ID NOS: 6

<210> SEQ ID NO 1
<211> LENGTH: 119
<212> TYPE: PRT
<213> ORGANISM: Artificial Sequence
<220> FEATURE:
<223> OTHER INFORMATION: variable region of the TRL1068 heavy chain

<400> SEQUENCE: 1

Gln Val Gln Leu Val Glu Ser Gly Pro Gly Leu Val Lys Pro Ser Glu
1               5                   10                  15

Thr Leu Ser Leu Thr Cys Arg Val Ser Gly Asp Ser Asn Arg Pro Ser
            20                  25                  30
```

```
Tyr Trp Ser Trp Ile Arg Gln Ala Pro Gly Lys Ala Met Glu Trp Ile
        35                  40                  45

Gly Tyr Val Tyr Asp Ser Gly Val Thr Ile Tyr Asn Pro Ser Leu Lys
    50                  55                  60

Gly Arg Val Thr Ile Ser Leu Asp Thr Ser Lys Thr Arg Phe Ser Leu
65                  70                  75                  80

Lys Leu Thr Ser Val Ile Ala Ala Asp Thr Ala Val Tyr Tyr Cys Ala
                85                  90                  95

Arg Glu Arg Phe Asp Arg Thr Ser Tyr Lys Ser Trp Trp Gly Gln Gly
                100                 105                 110

Thr Gln Val Thr Val Ser Ser
        115
```

```
<210> SEQ ID NO 2
<211> LENGTH: 116
<212> TYPE: PRT
<213> ORGANISM: Artificial Sequence
<220> FEATURE:
<223> OTHER INFORMATION: the variable region of the heavy chain of
      TRL1330

<400> SEQUENCE: 2

Gln Val Gln Leu Val Glu Ser Gly Thr Glu Val Lys Asn Pro Gly Ala
1               5                   10                  15

Ser Val Lys Val Ser Cys Thr Ala Ser Gly Tyr Lys Phe Asp Glu Tyr
                20                  25                  30

Gly Val Ser Trp Val Arg Gln Ser Pro Gly Gln Gly Leu Glu Trp Met
        35                  40                  45

Gly Trp Ile Ser Val Tyr Asn Gly Lys Thr Asn Tyr Ser Gln Asn Phe
    50                  55                  60

Gln Gly Arg Leu Thr Leu Thr Thr Glu Thr Ser Thr Asp Thr Ala Tyr
65                  70                  75                  80

Met Glu Leu Thr Ser Leu Arg Pro Asp Asp Thr Ala Val Tyr Tyr Cys
                85                  90                  95

Ala Thr Asp Lys Asn Trp Phe Asp Pro Trp Gly Pro Gly Thr Leu Val
                100                 105                 110

Thr Val Ser Ser
        115
```

```
<210> SEQ ID NO 3
<211> LENGTH: 120
<212> TYPE: PRT
<213> ORGANISM: Artificial Sequence
<220> FEATURE:
<223> OTHER INFORMATION: the variable region of the heavy chain of
      TRL1337

<400> SEQUENCE: 3

Gln Val Gln Leu Leu Glu Ser Gly Pro Gly Leu Val Lys Pro Ser Glu
1               5                   10                  15

Thr Pro Ser Leu Thr Cys Thr Val Ser Gly Gly Ser Ile Arg Ser Tyr
                20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Met Ser Lys Asn Gln Phe Ser Leu
65                  70                  75                  80
```

-continued

```
Lys Leu Ser Ser Val Thr Ala Ala Asp Thr Ala Met Tyr Tyr Cys Ala
                85                  90                  95

Arg Val Tyr Gly Gly Ser Gly Ser Tyr Asp Phe Asp Tyr Trp Gly Gln
            100                 105                 110

Gly Thr Leu Val Thr Val Ser Ser
        115                 120

<210> SEQ ID NO 4
<211> LENGTH: 108
<212> TYPE: PRT
<213> ORGANISM: Artificial Sequence
<220> FEATURE:
<223> OTHER INFORMATION: the variable region of the light chain of
      TRL1068

<400> SEQUENCE: 4

Asp Ile Val Leu Thr Gln Ala Pro Gly Thr Leu Ser Leu Ser Pro Gly
1               5                   10                  15

Asp Arg Ala Thr Leu Ser Cys Arg Ala Ser Gln Arg Leu Gly Gly Thr
            20                  25                  30

Ser Leu Ala Trp Tyr Gln His Arg Ser Gly Gln Ala Pro Arg Leu Ile
        35                  40                  45

Leu Tyr Gly Thr Ser Asn Arg Ala Thr Asp Thr Pro Asp Arg Phe Ser
    50                  55                  60

Gly Ser Gly Ser Gly Thr Asp Phe Val Leu Thr Ile Ser Ser Leu Glu
65                  70                  75                  80

Pro Glu Asp Phe Ala Val Tyr Tyr Cys Gln Gln Tyr Gly Ser Pro Pro
                85                  90                  95

Tyr Thr Phe Gly Gln Gly Thr Thr Leu Asp Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: the variable region of the light chain of
      TRL1330

<400> SEQUENCE: 5

Asp Ile Val Leu Thr Gln Ser Pro Ser Ala Ser Gly Ser Pro Gly Gln
1               5                   10                  15

Ser Ile Thr Ile Ser Cys Thr Gly Thr Asn Thr Asp Tyr Asn Tyr Val
            20                  25                  30

Ser Trp Tyr Gln His His Pro Gly Lys Ala Pro Lys Val Ile Ile Tyr
        35                  40                  45

Asp Val Lys Lys Arg Pro Ser Gly Val Pro Ser Arg Phe Ser Gly Ser
    50                  55                  60

Arg Ser Gly Asn Thr Ala Thr Leu Thr Val Ser Gly Leu Gln Thr Glu
65                  70                  75                  80

Asp Glu Ala Asp Tyr Tyr Cys Val Ser Tyr Ala Asp Asn Asn His Tyr
                85                  90                  95

Val Phe Gly Ser Gly Thr Lys Val Thr Val Leu
            100                 105

<210> SEQ ID NO 6
<211> LENGTH: 111
<212> TYPE: PRT
<213> ORGANISM: Artificial Sequence
```

-continued

```
<220> FEATURE:
<223> OTHER INFORMATION: the variable region of the light chain of
      TRL1337

<400> SEQUENCE: 6

Asp Ile Val Leu Thr Gln Ser Pro Ser Ala Ser Gly Ser Pro Gly Gln
1               5                   10                  15

Ser Val Thr Ile Ser Cys Thr Gly Thr Ser Ser Asp Val Gly Gly Tyr
                20                  25                  30

Asn Tyr Val Ser Trp Tyr Gln Gln Leu Pro Gly Lys Ala Pro Lys Leu
        35                  40                  45

Met Ile Tyr Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Phe Ala Gly Ser
                85                  90                  95

Asn Asn His Val Val Phe Gly Gly Gly Thr Lys Leu Thr Val Leu
            100                 105                 110
```